(12) United States Patent
Noyes

(10) Patent No.: US 11,478,130 B2
(45) Date of Patent: Oct. 25, 2022

(54) ENDOSCOPE WITH INTEGRATED ATTACHMENT MECHANISMS AND METHODS OF USE

(71) Applicant: ResnENT, LLC, Bloomington, IL (US)

(72) Inventor: Willard S. Noyes, Bloomington, IL (US)

(73) Assignee: RESNENT, LLC, Bloomington, IL (US)

( * ) Notice: Subject to any disclaimer, the term of this patent is extended or adjusted under 35 U.S.C. 154(b) by 0 days.

(21) Appl. No.: 17/503,044

(22) Filed: Oct. 15, 2021

(65) Prior Publication Data

US 2022/0117465 A1   Apr. 21, 2022

Related U.S. Application Data

(60) Provisional application No. 63/092,733, filed on Oct. 16, 2020.

(51) Int. Cl.
| | | |
|---|---|---|
| *A61B 1/00* | (2006.01) | |
| *A61B 1/005* | (2006.01) | |
| *A61B 1/008* | (2006.01) | |

(52) U.S. Cl.
CPC ...... *A61B 1/00128* (2013.01); *A61B 1/00006* (2013.01); *A61B 1/008* (2013.01);
(Continued)

(58) Field of Classification Search
CPC .............. A61B 1/00073; A61B 1/0014; A61B 1/00128
See application file for complete search history.

(56) References Cited

U.S. PATENT DOCUMENTS 5,156,141 A    10/1992  Krebs et al.
5,797,836 A *   8/1998  Lucey ..................... A61B 1/05
                                                          600/173
(Continued)

FOREIGN PATENT DOCUMENTS

WO    WO 2017/029156    2/2017

OTHER PUBLICATIONS

Invitation to Pay Additional Fees and Provisional Opinion Accompanying the Partial Search Result dated Jan. 11, 2022 for International Application No. PCT/US2021/055249, filed on Oct. 15, 2021.
(Continued)

*Primary Examiner* — Matthew J Kasztejna
(74) *Attorney, Agent, or Firm* — Sheppard, Mullin, Richter & Hampton LLP

(57) ABSTRACT

Some implementations of the disclosure relate to an endoscope, comprising: a shaft comprising: a distal end; and a proximal end comprising a rigid attachment segment configured to be removably coupled to an adapter or instrument, a surface of the rigid attachment segment comprising: a groove and a section adjacent the groove, the section protruding relative to the groove and comprising a recessed indentation or protrusion; and a housing coupled to the shaft. The surface of the rigid attachment segment may include multiple grooves and multiple sections alternating along the longitudinal length of the rigid attachment segment; each of the sections protrudes relative to the grooves and comprises a recessed indentation or protrusion; and the multiple sections and the multiple grooves are configured such that the instrument or the adapter can be coupled to the endoscope in a plurality of lengthwise positions.

20 Claims, 28 Drawing Sheets

(52) U.S. Cl.
CPC ........ *A61B 1/00009* (2013.01); *A61B 1/0014* (2013.01); *A61B 1/0051* (2013.01); *A61B 1/00073* (2013.01); *A61B 1/00119* (2013.01); *A61B 1/00121* (2013.01); *A61B 1/00147* (2013.01); *A61B 2217/005* (2013.01); *A61B 2217/007* (2013.01)

(56) References Cited

U.S. PATENT DOCUMENTS

| | | | |
|---|---|---|---|
| 6,991,602 | B2 | 1/2006 | Nakazawa et al. |
| 7,976,458 | B2 * | 7/2011 | Stefanchik ......... A61B 1/00154 |
| | | | 600/114 |
| 2004/0230096 | A1 | 11/2004 | Stefanchik et al. |
| 2005/0049459 | A1 | 3/2005 | Hern |
| 2005/0119524 | A1 | 6/2005 | Sekine et al. |
| 2005/0228224 | A1 | 10/2005 | Okada et al. |
| 2007/0225562 | A1 * | 9/2007 | Spivey ................ A61B 1/0052 |
| | | | 600/121 |
| 2008/0058595 | A1 | 3/2008 | Snoke et al. |
| 2008/0281299 | A1 | 11/2008 | Menn |
| 2018/0303314 | A1 | 10/2018 | Noyes |
| 2019/0167075 | A1 * | 6/2019 | Fischer ................ A61B 1/0055 |

OTHER PUBLICATIONS

Non-final Office Action dated Mar. 9, 2022 for U.S. Appl. No. 17/503,004, filed Oct. 15, 2021.
International Search Report and Written Opinion dated May 20, 2022 for International Application No. PCT/US2021/055249, filed Oct. 15, 2021.
Final Office Action dated Jun. 8, 2022 for U.S. Appl. No. 17/503,004, filed Oct. 15, 2021.

* cited by examiner

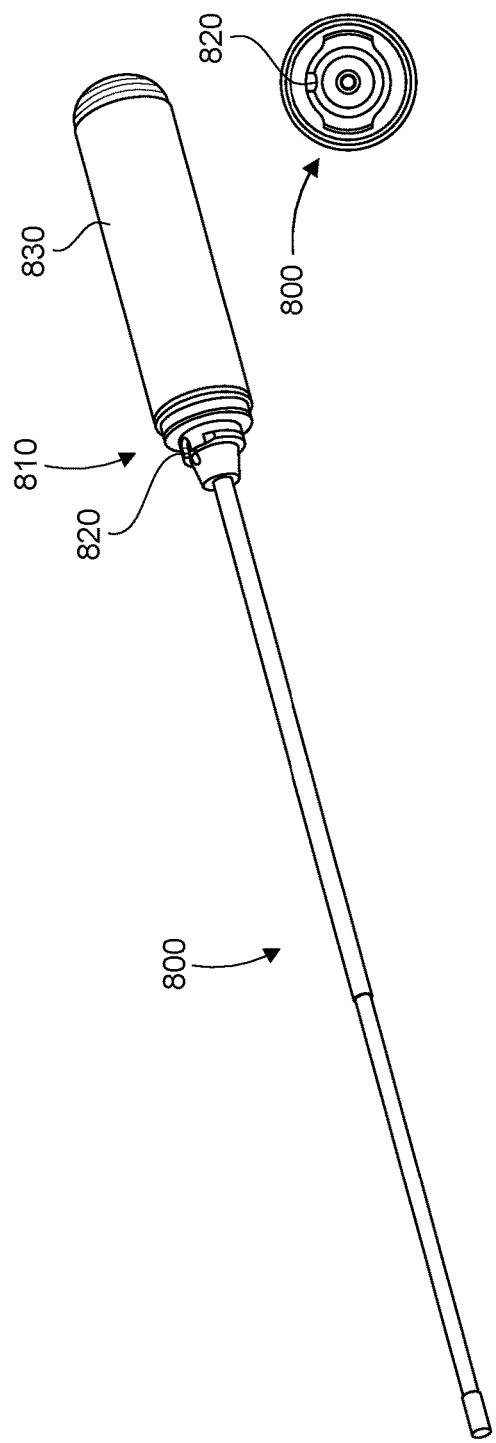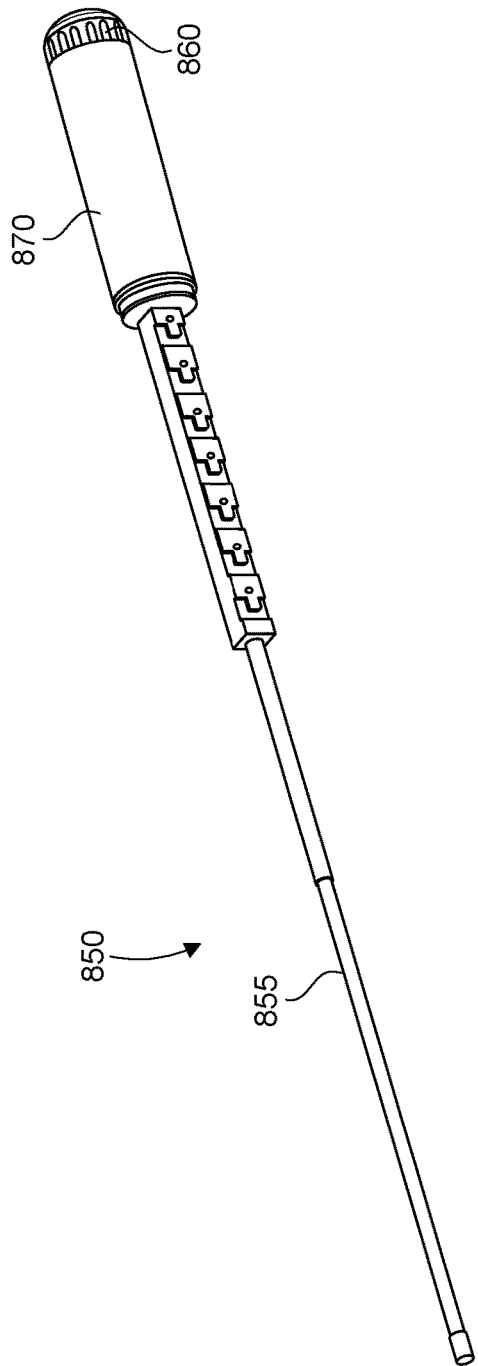
FIG. 8A
FIG. 8B

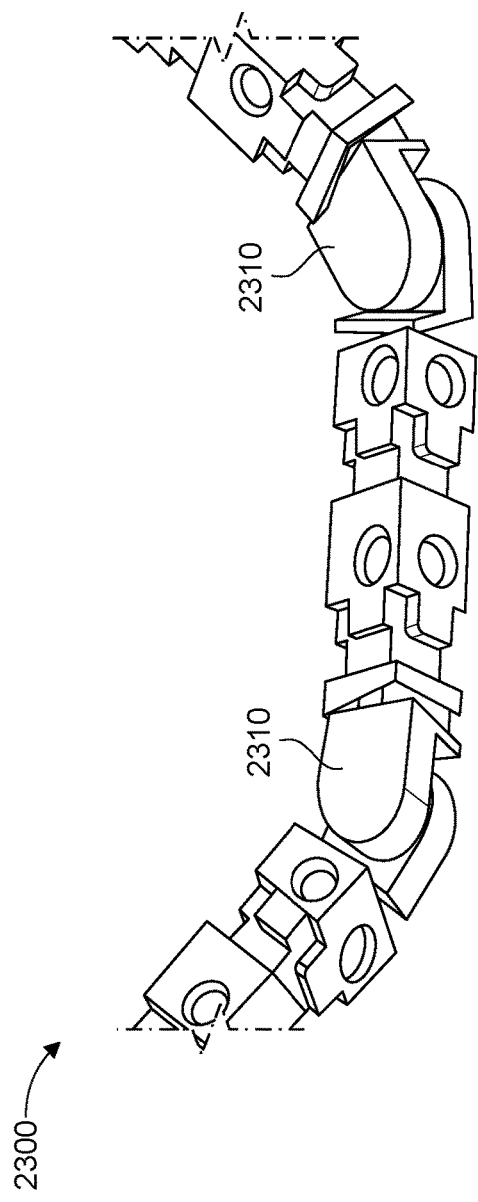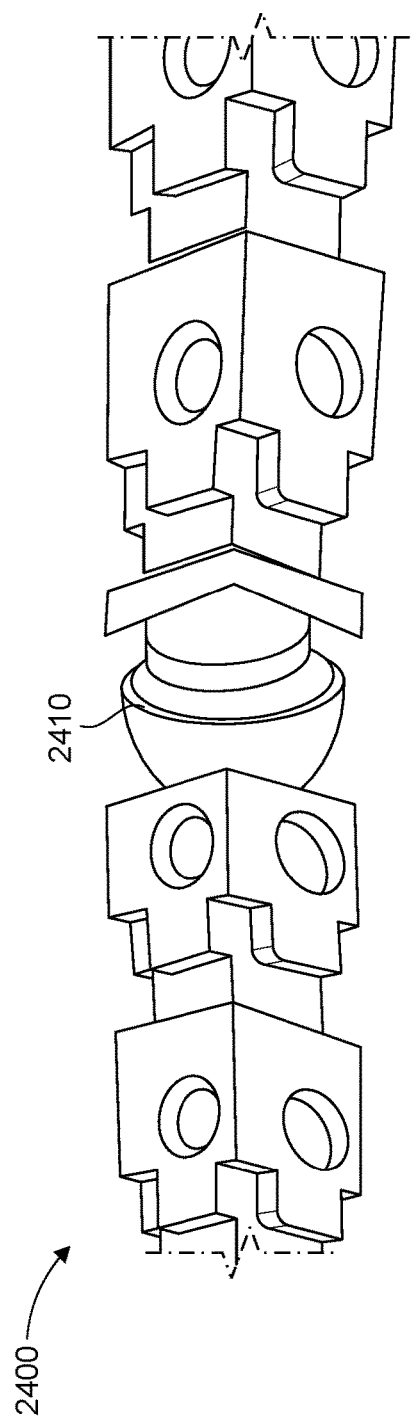

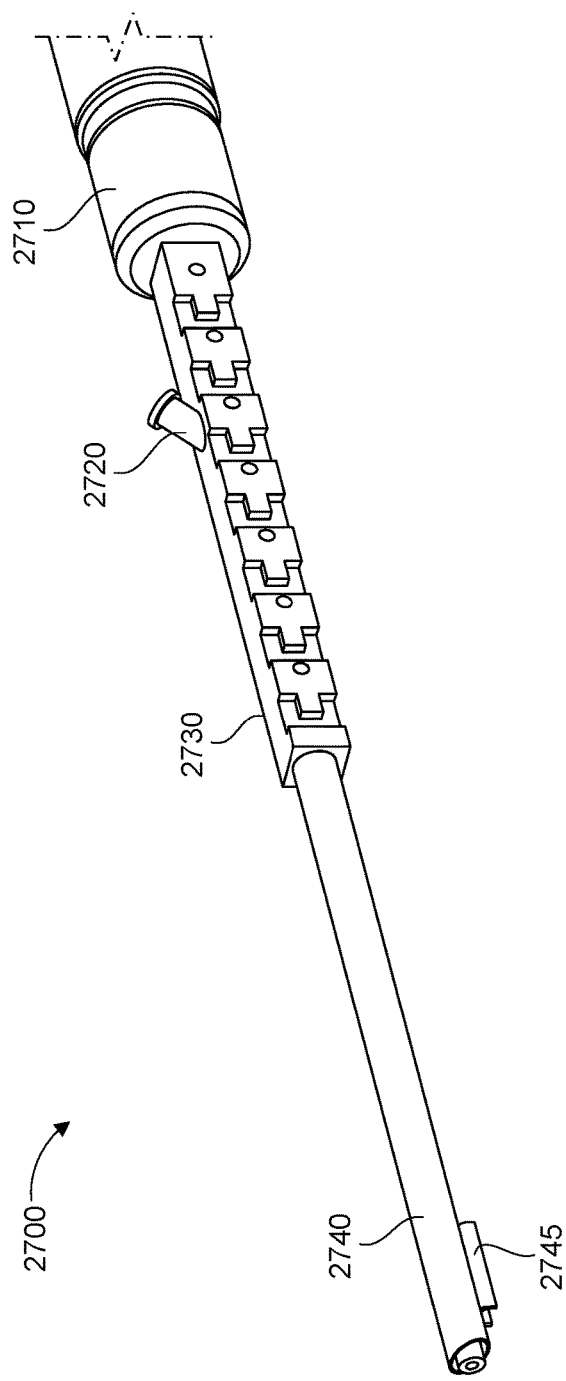
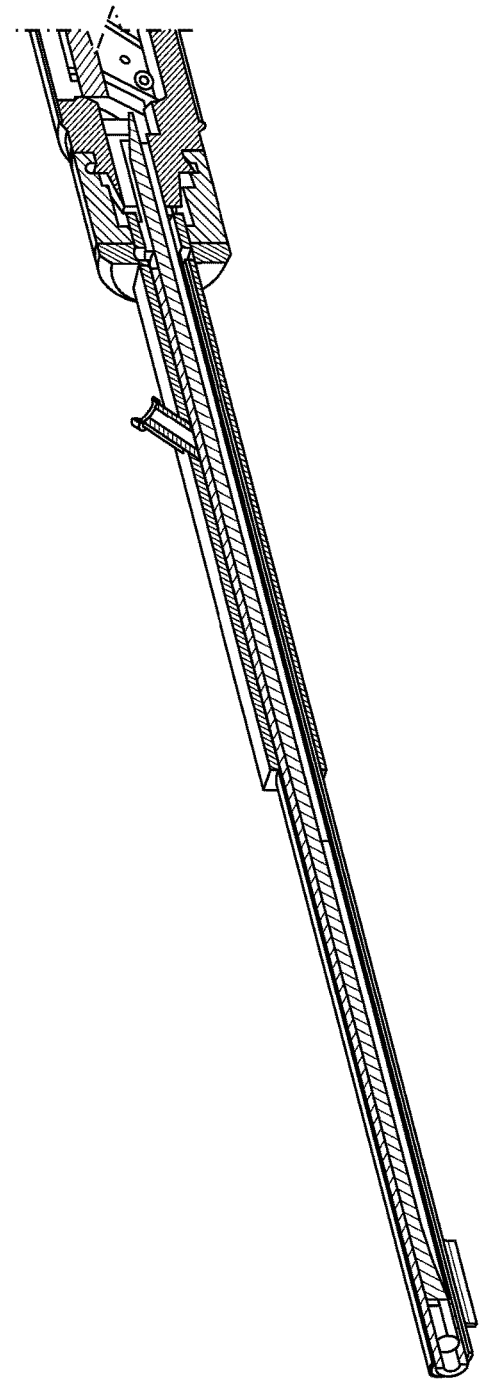
FIG. 27A
FIG. 27B

ENDOSCOPE WITH INTEGRATED ATTACHMENT MECHANISMS AND METHODS OF USE

CROSS-REFERENCE TO RELATED APPLICATIONS

This application claims priority to U.S. Provisional Application No. 63/092,733 filed Oct. 16, 2020 and titled "ENDOSCOPE ATTACHMENT MECHANISMS AND METHODS OF USE," which is incorporated herein by reference in its entirety.

BACKGROUND

Endoscopes are illuminated tubular instruments with eyepieces or cameras that are used to look inside a body cavity in procedures called an endoscopy. During performance of a medical procedure with an instrument that is inserted within a patient's body cavity, endoscopes may be used to visualize the medical instrument and body cavity during the procedure. For example, the endoscope may be used to allow the physician to view tissue or other matter within a cavity or anatomic space in a patient while using suction or grasping forceps to remove tissue from the space.

In procedures that utilize medical instruments in combination with endoscopes, the endoscope is typically a rigid or flexible tool that is manipulated separately from the medical instrument. During the procedure, medical personnel hold and guide the endoscope with one hand and the instrument used to treat the patient with the other hand. Depending on the anatomic space to be visualized, physicians will use either a rigid or flexible endoscope. For example, pulmonologists and gastroenterologists use flexible endoscopes and orthopedic surgeons typically use rigid endoscopes, whereas otolaryngologists use either rigid or flexible scopes depending on the surgical application. When using endoscopes with other surgical instrumentation within a confined space, there is often interference between the endoscope and instrument when trying to manipulate within the same anatomic space. This is sometimes referred to as "sword fighting" and can make surgeries technically more difficult and sometimes require another incision or access port to overcome. This is particularly true in orthopedic arthroscopy or when operating in the posterior nasal cavity.

Current implementations of rigid endoscopes have significant limitations with respect to visualizing the patient's body cavity during a procedure. Angled rigid scope visualization often distorts the surgeon's perspective and is cumbersome to use in conjunction with secondary instruments. The surgeon is often handicapped by the rigidity of the endoscope and the angle of visualization when trying to perform tasks in small cavities or in areas difficult to reach with instruments. This is particularly true when trying to operate within the frontal and maxillary sinuses. In pediatric cases, there is often not enough room to insert multiple instruments into a nasal passage or sinus opening at the same time. In addition, during direct laryngoscopy procedures, multiple instruments inserted into the lumen of a rigid laryngoscope makes direct visualization around the endoscope, camera attachment, and instrumentation very difficult.

Likewise, current implementations of flexible endoscopes present their own set of problems. In some current flexible endoscopic systems on the market, a tool is advanced through a tiny instrument channel incorporated within the length of a flexible endoscope. In such systems, the size of the tool is limited to the diameter of the endoscopic channel, and thus greatly limits the tool sizes and options available for endoscopic tissue manipulation. Externally attaching a conventional flexible endoscope to a surgical instrument or device is difficult because the endoscope body is difficult to stabilize, the endoscope hangs off the back of the instrument, and the endoscope does not connect or transfer easily from one instrument to another. Use of currently available flexible endoscopes requires two hands: one hand to manipulate the tip flexion and another hand to stabilize the tip the flexible shaft.

As noted above, current implementations of endoscopes have limitations with respect to their usage with other instruments during procedures. Rigid endoscopes cannot be bent to effectively visualize a body cavity of the patient, and flexible endoscopes cannot be effectively stabilized or easily used in combination with other internal or externally applied instrumentation. In many cases, it may be difficult for the endoscope to visualize the grasping or removing of tissues, and in some hard to reach areas such as the maxillary and frontal sinuses, such a procedure is often done blindly, resulting in incomplete tissue removal.

In order to overcome some of these limitations in flexible and rigid endoscope design and functionality, U.S. Pat. No. 10,512,391 introduced an improved flexible-rigid hybrid design for an endoscope with instrument attachment capabilities for removably coupling and decoupling the endoscope to a proximal handle portion and/or a distal tool portion of a variety of different surgical instruments. The remains however continued need for newer and simplified methods for attachment of endoscopes to various surgical instruments across numerous surgical specialties.

SUMMARY OF INVENTION

The current disclosure describes different attachment mechanisms for attaching an endoscope shaft to various instrumentation. The manner in which an endoscope shaft can be modified, either permanently or temporarily to allow for quick attachment to an instrument (e.g., surgical tool) is further detailed below. Additionally, various adapters are presented that would facilitate attachment of the endoscope shafts to surgical instrumentation. Different instrument types and the modifications necessary to allow endoscope attachment are also provided.

There is a need for improved mechanisms for attaching different types of endoscopes to instruments. To this end, implementations of the present disclosure are directed toward endoscope shaft design and attachment adapters that may be removably or permanently coupled to an endoscope or surgical instrument in a variety of manners and configurations.

As further described below, an endoscope shaft attachment adapter may be advanced over the shaft of the endoscope and secured at a proximal end of the endoscope shaft (e.g., by connecting it to the distal end of the endoscope handle/scope head). This endoscope attachment "sleeve" adapter includes a rigid attachment segment including means for coupling the endoscope to an instrument in a plurality of lengthwise positions. The endoscope attachment adapter may also be configured such that the endoscope may be attached to the instrument in a plurality of different circumferential positions. For example, the endoscope attachment adapter may be configured to rotate about its longitudinal axis, and/or the endoscope attachment adapter may have attachment means circumferentially spaced about the rigid attachment segment.

Although the channel housing attachment mechanism described in U.S. Pat. No. 10,512,391 is functional and most often adequate, it can allow for excess movement of the scope within the channel secondary to inherent play in the movement of the lever arm as it engages with the scope. In addition, it may require an excessively elongated channel to accommodate the mechanical action and length of a side button and scope engagement lever.

Initially described for use with a hybrid, rigid/flexible endoscope, the ability to adapt conventional rigid or flexible endoscopes to work with the attachment mechanism described in U.S. Pat. No. 10,512,391 would be advantageous. Prior disclosure shows the slotted/grooved, rectangular, proximal attachment portion of the endoscope shaft to be a rigid extension of the endoscope housing. Endoscopes of conventional design that do not contain this proximal shaft attachment configuration typically have a smooth, circumferential shaft making attachment to instrumentation difficult. Such conventional endoscopes would require an adapter sleeve to convert the smooth endoscope shaft to a shape and configuration that would allow attachment to instrumentation in a manner similar to that previously described. These attachment adapter sleeves could slide over the smooth endoscope shaft and fixate to the endoscope housing via a coupler. Different embodiments may require sleeve adapters that are rigid, malleable, articulating, or flexible.

When externally attaching an endoscope to a surgical device, the orientation of the image in relation to the scope and instrument handle must be maintained or adjusted as necessary to maintain adequate user display orientation. If the user rotates the handle position then the image will rotate accordingly because the endoscope is fixated to the instrument devise. Having the ability to mechanically rotate and reorient an image while an endoscope is fixated to a surgical tool via the attachment mechanisms described herein would also be beneficial. Such applications would require the endoscope shaft, whether rigid, flexible, or hybrid, to circumferentially rotate within the sleeve adapter depending on the application.

The present disclosure also includes scope shafts that are either removably or permanently fixed to the endoscope housing. Such endoscopes and endoscope shaft configurations could be made disposable or remain reusable and would contain the optical and mechanical configurations necessary to allow instrument attachment and transference of the optical signal from the distal tip of the endoscope through to the proximal endoscope housing. Removable shafts, sleeve adapters, or permanent shaft designs that act to alter the shape, angulation, or configuration of the scope shaft, convert a flexible scope shaft (or portion thereof) to a more rigid scope shaft, or convert a flexible or hybrid shaft into a hinged shaft utilizing single or multiple hinged units are also envisioned. A hinged endoscope, created either as a one-piece fabricated unit or the result of a removable hinged shaft or hinged sleeve adapter would allow adjustable angulation of the endoscope housing away from the long axis of the endoscope shaft, such as would be required during direct operative laryngoscopy. A hinged shaft design might also enable scope rotation within the lumen of the hinged shaft or adapter.

Endoscope shafts of customized shape and contour might be useful when attaching the endoscope to various surgical instrument housings or devices. Such devices may include surgical coblation or plasma wands, inflation balloons, electrocautery devices, lasers, cannulas, syringes, robotic tools, articulating forceps, articulating cannulas, ultrasound probes, surgical staplers, snares, etc. The irregular shape or contour of these instrument devices/housings could impede attachment of the endoscope shaft and attached endoscope housing to the instrument and therefore interfere with proper instrument use, mechanics, or line of sight visualization. Significant re-engineering of existent instrument devices with profiles unable to accommodate the linear nature of the endoscope may need to occur.

Re-engineering expenses may prohibit instrument manufacturers from making necessary design modifications to allow for endoscope attachment. A channel adapter that is capable of receiving and securing the endoscope shaft both proximally and/or distally could be clipped to such devices in a customized manner and would make this endeavor more feasible and cost effective.

By virtue of using the endoscope attachment adapters described herein, various technical advantages may be realized. First, the adapters may be used to retrofit existing endoscopes, rigid or flexible, with a rigid attachment segment. The adapter, when retrofitted over the endoscope, may provide for improved and simplified mechanism for removably coupling and decoupling the endoscope to a variety of different instruments. For example, the adapter may be retrofitted over an existing flexible endoscope to convert it to a flexible-rigid hybrid endoscope having the benefits of a flexible distal shaft segment and rigid proximal shaft segment with an instrument attachment mechanism.

The retrofitted adapter may provide a variety of advantages to both physicians and patients. For example, by providing a quick, simplified, and reliable mechanism for removably coupling an endoscope to an instrument, the adapter may save the physician and patient time. Additionally, the adapters described herein may be adapted to be removably coupled to a variety of different instrument types, which may provide additional cost savings and convenience. It may allow for the physician to use an endoscope with a variety of different instruments in a one-handed manner to facilitate a patient procedure. Removable, disposable endoscope and adapter shaft configurations would avoid the need for repeat sterilization and therefore increase operating room efficiency and case turn around. In some cases, this may eliminate the requirement of having a second medical person to help with the procedure, and may permit more office-based surgeries, which may reduce the cost of various procedures.

Further still, the adapter designs and shaft configurations described herein may improve patient comfort by eliminating the need to separately insert an endoscope and instrument into a body orifice (e.g., nose or throat) at the same time. Moreover, the adapter design may improve surgical access, visualization, and instrumentation within conventionally hard to reach anatomic places such as the nasopharynx, frontal sinus, anterior maxillary sinus, tongue base, orthopedic joint space, uterus, abdomen, bladder, etc.

In further implementations, the rigid attachment segment of the endoscope shaft or sleeve adapter may include an improved design for engaging the endoscope in an instrument channel.

In yet further implementations, the rigid attachment segment of the shaft or sleeve adapter may be hinged, allowing for changes in the shape of the rigid shaft to accommodate varying shapes and contours of surgical instruments without allowing for flaccidity which would destabilize the scope when attached to an instrument.

In yet further implementations, sleeve adapters to provide suction and/or irrigation to the endoscope tip or to facilitate attachment of the distal aspect of an endoscope shaft, whether flexible or rigid, to an instrument or instrument shaft are also described.

In yet further implementations, a disposable and/or removable rigid, flexible, or hybrid endoscope shaft may insert into an otherwise disposable or reusable endoscope housing or rigid attachment segment extending from the housing. The disposable shafts may include various instrument channel connectors for the attachment of external instrument configurations to the distal or proximal endoscope shaft. In other embodiments, the removable endoscope shafts may include other adapter features described herein. For example, suction or irrigation channels may be incorporated into the removable shaft. Some disposable shafts might be hinged, malleable, articulating, or irregularly contoured, etc. Combining one or more adapter features into an disposable endoscope shaft that is instrument attachable may obviate the need to utilize additional adapters.

In one embodiment an adapter comprises: a channel running through the length of the adapter from a first opening at a distal end of the adapter to a second opening at a proximal end of the adapter, wherein a shaft of an endoscope is configured to be threaded through the channel; a first coupler configured to removably secure the adapter to a second coupler of the endoscope after the shaft is threaded through the channel, the first coupler comprising the second opening; and a rigid attachment segment comprising a surface configured to removably couple the adapter to an instrument or a second adapter.

In some implementations, the surface of the rigid attachment segment comprises a groove and a section adjacent the groove, the section protruding relative to the groove and comprising a recessed indentation or protrusion. In some implementations, the surface of the rigid attachment segment comprises multiple grooves and multiple sections alternating along the longitudinal length of the rigid attachment segment; each of the sections protrudes relative to the grooves and comprises a recessed indentation or protrusion; and the multiple sections and the multiple grooves are configured such that the instrument or the second adapter can be coupled to the adapter in a plurality of lengthwise positions.

In some implementations, the adapter further comprises: a rotatable joint attached to the rigid attachment segment and configured to enable longitudinal rotation of the rigid attachment segment relative to the first coupler. The rotatable joint may comprise multiple apertures circumferentially arranged on a periphery of an inner surface of the rotatable joint, wherein the rotatable joint is configured to be secured in an angular position by a block pressed into one of the apertures. The block may be pressed into one of the apertures by a spring contained within a housing of the coupler, wherein rotation of the rigid attachment segment relative to the first coupler with a sufficient torque is configured to cause the block to compress the spring and release the block from one of the apertures. In some implementations, the rotatable joint comprises: a circular extension configured to engage the first connector, the circular extension comprising a first circumferential lip that engages a wider circumferential lip within the first coupler.

In some implementations, the rigid attachment segment has at least two different surfaces running along a longitudinal length of the rigid attachment segment, wherein each of the at least two different surfaces comprise: a groove and a section adjacent the groove, the section protruding relative to the groove and comprising a recessed indentation or protrusion. In some implementations, the rigid attachment segment has at least two different surfaces running along a longitudinal length of the rigid attachment segment, wherein each of the at least two different surfaces comprises: multiple grooves and multiple sections alternating along the longitudinal length of the rigid attachment segment, wherein each of the sections protrudes relative to the grooves and comprises a recessed indentation or protrusion, and the multiple sections and the multiple grooves are configured such that the instrument or the second adapter can be coupled to the surface in a plurality of lengthwise positions.

In some implementations, the rigid attachment segment is configured to be fixed relative to the first coupler.

In some implementations, the adapter further comprises: a distal segment comprising the first opening, wherein the distal segment is configured to stabilize the endoscope and the adapter after the adapter is removably coupled to the endoscope.

In some implementations, a distal end of the rigid attachment segment comprises the first opening.

In some implementations, the second coupler comprises a groove, and the first coupler comprises: a locking screw configured to be threaded into the groove to secure the first coupler to the second coupler; a slidable control configured to slide into the groove of the second coupler to secure the first coupler to the second coupler; or a button coupled to a lever arm, the button configured to be actuated to engage the lever arm into the groove to secure the first coupler to the second coupler.

In some implementations, the rigid attachment segment comprises a hinged joint between two portions of the rigid attachment segment, the hinged joint configured to enable pivoting or rotation of at least one of the two portions about at least one plane.

In some implementations, the adapter further comprises: a hinged joint between the rigid attachment segment and the first coupler, the hinged joint configured to enable pivoting or rotation of the rigid attachment segment.

In some implementations, the adapter further comprises: an integrated cannula, the cannula comprising a suction or irrigation port.

In one embodiment, an endoscope attachment assembly, comprises: an endoscope comprising a shaft and a housing, the housing comprising a first coupler at its distal end; and a first adapter comprising: a channel running through the length of the adapter from a first opening at a distal end of the adapter to a second opening at a proximal end of the adapter, wherein the shaft of the endoscope is configured to be threaded through the channel; a second coupler configured to removably secure the adapter to the first coupler of the endoscope after the shaft is threaded through the channel, the second coupler comprising the second opening; and a rigid attachment segment comprising a surface configured to removably couple the adapter to an instrument or a second adapter.

In some implementations, the first adapter of the endoscope attachment assembly is any of the aforementioned adapters.

In some implementations, the endoscope attachment assembly further comprises: the second adapter, the second adapter comprising a first channel configured to be removably coupled to the rigid attachment segment, and a second channel configured to be removably coupled to an instrument.

In some implementations, the surface of the rigid attachment segment comprises a groove and a section adjacent the groove, the section protruding relative to the groove and comprising a recessed indentation or protrusion, and an interior surface of the first channel comprises a protrusion configured to engage the groove, and a spring-loaded ball configured to engage the recessed indentation of the section.

In some implementations, the surface of the rigid attachment segment comprises multiple grooves and multiple sections alternating along the longitudinal length of the rigid attachment segment; each of the sections protrudes relative to the grooves and comprises a recessed indentation or protrusion; and the multiple sections and the multiple grooves are configured such that the instrument or the second adapter can be coupled to the adapter in a plurality of lengthwise positions, wherein an interior surface of the first channel comprises two protrusions and a spring-loaded ball, wherein the rigid attachment segment is configured to be secured to the second adapter by placing the rigid attachment segment into the first channel and sliding the rigid attachment segment relative to the first channel such that two of the grooves of the rigid attachment segment are secured by the two protrusions and the spring-loaded ball is secured in one of the recessed indentations.

In some implementations, the second adapter is an H-channel adapter, wherein one of the first and second channel is a top open channel of the H-channel adapter, and one of the first channel and second channels is a lower open channel of the H-channel adapter.

In some implementations, the endoscope attachment assembly further comprises: the instrument, the instrument comprising: a channel configured to be removably coupled to the rigid attachment segment.

In some implementations, the surface of the rigid attachment segment comprises a groove and a section adjacent the groove, the section protruding relative to the groove and comprising a recessed indentation or protrusion, wherein an interior surface of the instrument's channel comprises a protrusion configured to engage the groove, and a spring-loaded ball configured to engage the recessed indentation of the section.

In some implementations, the surface of the rigid attachment segment comprises multiple grooves and multiple sections alternating along the longitudinal length of the rigid attachment segment; each of the sections protrudes relative to the grooves and comprises a recessed indentation or protrusion; and the multiple sections and the multiple grooves are configured such that the instrument or the second adapter can be coupled to the adapter in a plurality of lengthwise positions, wherein an interior surface of the instrument's channel comprises two protrusions and a spring-loaded ball, wherein the rigid attachment segment is configured to be secured to the second adapter by placing the rigid attachment segment into the instrument's channel and sliding the rigid attachment segment relative to the instrument's such that two of the grooves of the rigid attachment segment are secured by the two protrusions and the spring-loaded ball is secured in one of the recessed indentations.

In some implementations, the endoscope comprises a rotatable control positioned at a proximal end of the endoscope, wherein the control is configured to be rotated to digitally adjust an orientation of an image captured by the endoscope.

In some implementations, the endoscope attachment assembly further comprises: the second adapter, the second adapter comprising a first channel configured to be removably coupled to the rigid attachment segment, and a second channel, the second channel comprising a plurality of clips configured to be removably coupled to an instrument.

In one embodiment, an endoscope comprises: a shaft comprising: a distal end; and a proximal end comprising a rigid attachment segment configured to be removably coupled to an instrument, a surface of the rigid attachment segment comprising: a groove and a section adjacent the groove, the section protruding relative to the groove and comprising a recessed indentation or protrusion; and a housing coupled to the shaft.

In some implementations, the surface of the rigid attachment segment comprises multiple grooves and multiple sections alternating along the longitudinal length of the rigid attachment segment; each of the sections protrudes relative to the grooves and comprises a recessed indentation or protrusion; and the multiple sections and the multiple grooves are configured such that the instrument can be coupled to the endoscope in a plurality of lengthwise positions.

In some implementations, the endoscope further comprises: a rotatable joint attached to the rigid attachment segment and configured to enable longitudinal rotation of the rigid attachment segment relative to the housing.

In some implementations, the rigid attachment segment has at least two different surfaces running along a longitudinal length of the rigid attachment segment, wherein each of the at least two different surfaces comprise: a groove and a section adjacent the groove, the section protruding relative to the groove and comprising a recessed indentation.

In some implementations, the rigid attachment segment has at least two different surfaces running along a longitudinal length of the rigid attachment segment, wherein each of the at least two different surfaces comprises: multiple grooves and multiple sections alternating along the longitudinal length of the rigid attachment segment, wherein each of the sections protrudes relative to the grooves and comprises a recessed indentation, and the multiple sections and the multiple grooves are configured such that the instrument can be coupled to the surface in a plurality of lengthwise positions.

In some implementations, the endoscope comprises a rotatable control positioned at a proximal end of the endoscope, wherein the control is configured to be rotated to digitally adjust an orientation of an image captured by the endoscope.

In some implementations, the rigid attachment segment comprises a hinged joint between two portions of the rigid attachment segment, the hinged joint configured to enable pivoting or rotation of at least one of the two portions about at least one plane.

In some implementations, the endoscope further comprises a hinged joint between the rigid attachment segment and the housing, the hinged joint configured to enable pivoting or rotation of the rigid attachment segment.

In some implementations, the endoscope further comprises an integrated cannula, the cannula comprising a suction or irrigation port.

In one embodiment, an adapter comprises: a closed first channel running through the length of the adapter from a first opening at a distal end of the adapter to a second opening at a proximal end of the adapter, wherein a shaft of an endoscope is configured to be threaded through the closed first channel; a channel housing comprising an open second channel, an interior of the open second channel comprising an attachment mechanism for removably coupling the adapter to an instrument; and a first coupler configured to removably secure the adapter to a second coupler of the endoscope after the shaft is threaded through the channel, the first coupler comprising the second opening.

In some implementations, the attachment mechanism comprises a protrusion configured to engage a groove of the instrument, and a spring-loaded ball configured to engage a recessed indentation of the instrument.

In some implementations, the adapter further comprises: a rotatable joint attached to the channel housing and configured to enable longitudinal rotation of the channel housing segment relative to the first coupler.

In one embodiment, an endoscope attachment assembly comprises: an endoscope comprising a shaft and a housing, the housing comprising a first coupler at its distal end; and an adapter, comprising: a closed first channel running through the length of the adapter from a first opening at a distal end of the adapter to a second opening at a proximal end of the adapter, wherein the shaft is configured to be threaded through the closed first channel; a channel housing comprising an open second channel, an interior of the open second channel comprising an attachment mechanism for removably coupling the adapter to an instrument; and a second coupler configured to removably secure the adapter to the first coupler after the shaft is threaded through the channel, the second coupler comprising the second opening.

In some implementations, the attachment mechanism comprises a protrusion configured to engage a groove of the instrument, and a spring-loaded ball configured to engage a recessed indentation of the instrument.

In some implementations, the endoscope attachment assembly comprises the instrument, the instrument comprising the handle, wherein the groove and the recessed indentation are on a handle of the instrument.

Other features and aspects of the disclosed technology will become apparent from the following detailed description, taken in conjunction with the accompanying drawings, which illustrate, by way of example, the features in accordance with implementations of the disclosed technology. The summary is not intended to limit the scope of any inventions described herein, which are defined by the claims and equivalents.

It should be appreciated that all combinations of the foregoing concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF THE DRAWINGS

The present disclosure, in accordance with one or more implementations, is described in detail with reference to the following figures. The figures are provided for purposes of illustration only and merely depict example implementations. Furthermore, it should be noted that for clarity and ease of illustration, the elements in the figures have not necessarily been drawn to scale.

Some of the figures included herein illustrate various implementations of the disclosed technology from different viewing angles. Although the accompanying descriptive text may refer to such views as "top," "bottom" or "side" views, such references are merely descriptive and do not imply or require that the disclosed technology be implemented or used in a particular spatial orientation unless explicitly stated otherwise.

FIG. 8A shows an endoscope with a twist-on male coupler attached to the endoscope head, in accordance with some implementations of the disclosure.

FIG. 8B shows an endoscope that contains a rotatable ring on the proximal part of the endoscope housing, in accordance with some implementations of the disclosure.

FIG. 23 shows a portion of an endoscope shaft or endoscope attachment adapter that is rectangular and includes hinged joints, in accordance with some implementations of the disclosure.

FIG. 24 shows a portion of an endoscope shaft or endoscope attachment adapter that includes a ball and socket hinge, in accordance with some implementations of the disclosure.

FIG. 27A shows a perspective view of an endoscope attachment adapter with an integrated cannula that may be used to flush or clean the tip of an endoscope, in accordance with some implementations of the disclosure.

FIG. 27B shows a cross-sectional view of the endoscope attachment adapter of FIG. 27A.

The figures are not exhaustive and do not limit the present disclosure to the precise form disclosed.

DETAILED DESCRIPTION

The present disclosure, in accordance with one or more implementations, is described in detail with reference to the following figures. The figures are provided for purposes of illustration only and merely depict example implementations. Furthermore, it should be noted that for clarity and ease of illustration, the elements in the figures have not necessarily been drawn to scale.

Some of the figures included herein illustrate various implementations of the disclosed technology from different viewing angles. Although the accompanying descriptive text may refer to such views as "top," "bottom" or "side" views, such references are merely descriptive and do not imply or require that the disclosed technology be implemented or used in a particular spatial orientation unless explicitly stated otherwise.

Figure 1A:
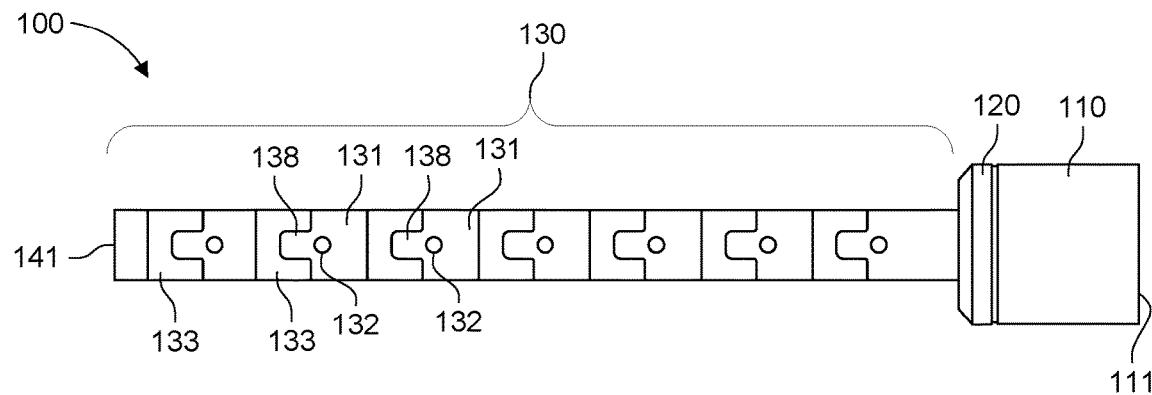
FIG. 1A shows a side view of an endoscope attachment adapter, in accordance with some implementations of the disclosure.
Figure 1B:
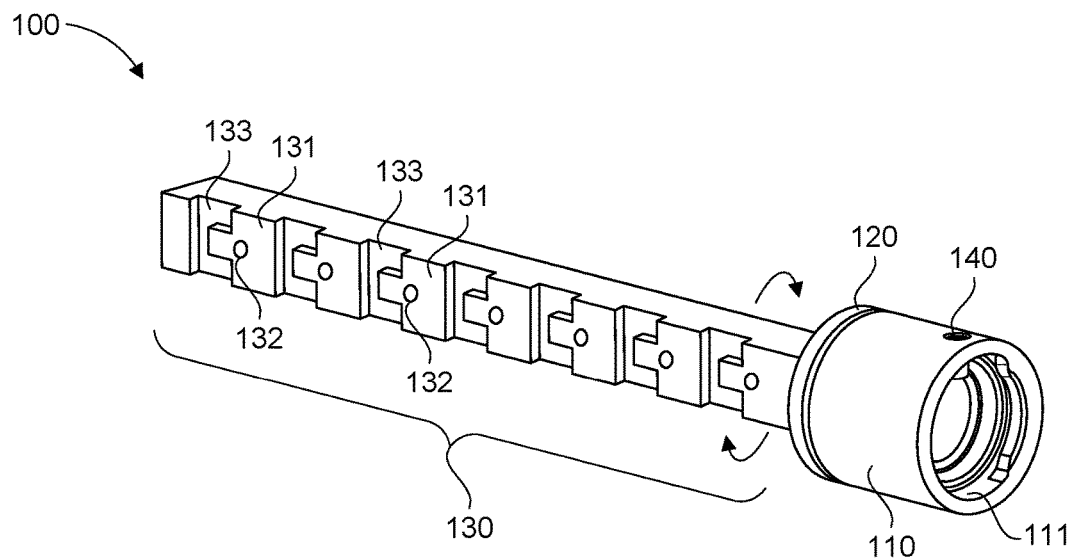
FIG. 1B shows a perspective view of the endoscope attachment adapter of FIG. 1A.
Figure 1C:
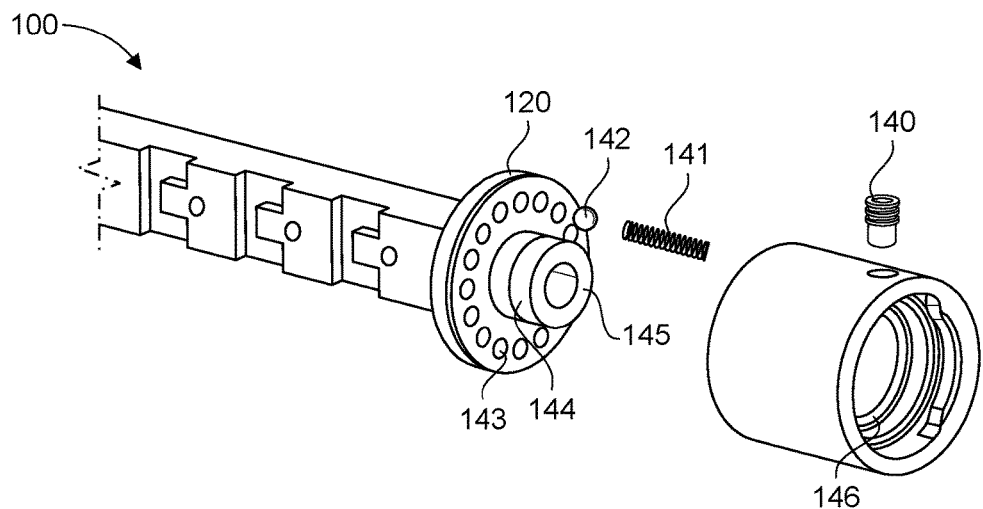
FIG. 1C shows an exploded perspective view of the endoscope attachment adapter of FIG. 1A.
Figure 1D:
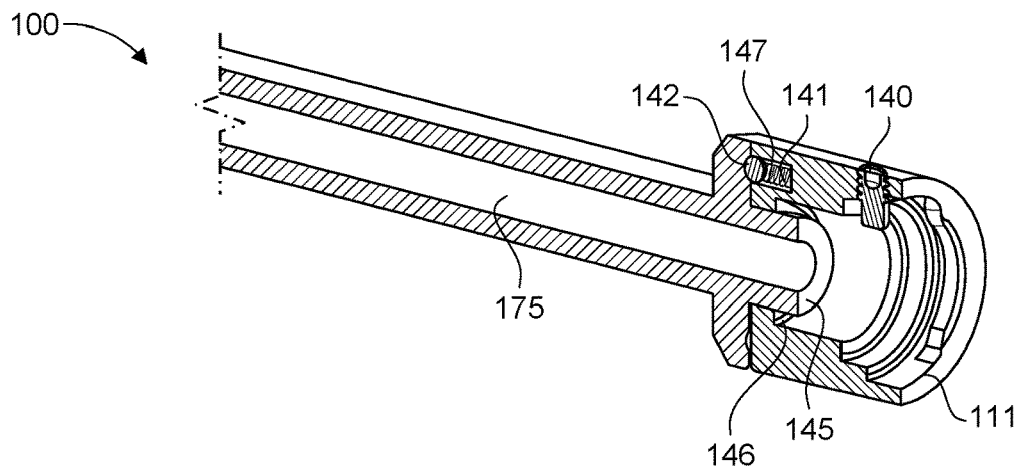
FIG. 1D shows a cross-sectional view of the endoscope attachment adapter of FIG. 1A.

FIGS. 1A-1D depict an endoscope attachment adapter 100, in accordance with implementations of the disclosure. FIG. 1A illustrates a side view of adapter 100, FIG. 1B illustrates a perspective view of adapter 100, FIG. 1C illustrates an exploded perspective view of adapter 100, and FIG. 1D illustrates a cross-sectional view of adapter 100. Adapter 100 includes a stationary coupler 110, a rotatable joint 120, and a rigid attachment segment 130.

At a proximal end of adapter 100 is an opening 111 through connector 110. At a distal end of adapter 100 is an opening 141. The opening 141 may begin at a distal end of rigid attachment segment 130. From opening 111 to opening 141 is a channel 175 that extends through coupler 110 and rigid attachment segment 130. A shaft of an endoscope may be threaded through channel 175, starting at opening 111 and moving through opening 141. Once the endoscope shaft is threaded through the channel of adapter 100, adapter 100 may be secured at a proximal end of the endoscope shaft by removably coupling adapter connector 110 (e.g., to an endoscope connector). The two connectors may be secured via one or more suitable coupling mechanisms, including a twist lock mechanism, an interference fit, a suction fit, a magnetic mechanism, and/or some other mechanism. Although in this example coupler 110 is illustrated as a female coupler configured to connect to a male coupler (e.g., at a proximal end of an endoscope shaft), in other implementations coupler 110 may be a male coupler configured to connect to a female coupler (e.g., at a proximal end of an endoscope shaft).

In this example, rigid attachment segment 130 is four-sided with a square cross section. In other implementations, rigid attachment segment 130 may have a different rectangular, circular, or other geometric cross section. On the surface of one of the four sides of segment 130 are formed a plurality of grooves/slots 133 and a plurality of sections 131 that protrude relative to the grooves 133, each of the sections 131 having a recessed indentation or hole 132. In this example, the plurality of grooves 133 and the plurality of sections 131 alternate along the longitudinal length of segment 130. As further described below, at least one groove 133 and at least one section 131 (e.g., a groove 133 adjacent a section 131) may be used to couple the adapter 100 to a channel of an instrument in a specific lengthwise position. In this manner, an endoscope with a secured adapter 100 may be coupled to a channel of an instrument in a specific lengthwise position. The number of grooves 133 and the number of sections 131 may depend on the desired number of lengthwise adjustments for coupling adapter 100 to an instrument, and the increment of each lengthwise adjustment. The number of grooves 133 and number of sections 131 may also depend on the width of each groove 133 and the width of each section 131. In some implementations, rigid attachment segment 130 may have between 1 and 30 grooves 133, and between 1 and 30 sections 131. In some implementations, to provide a more secure connection between the endoscope shaft (with adapter) and an instrument, multiple grooves 133 and multiple segments 131 may be used to connect to the instrument. Although grooves 133 and sections 131 are formed only on one side of segment 130 in this example, in other implementations, further described below they may be formed on two, three, or all four sides.

In alternative implementations, rigid attachment segment 130 may utilize some other suitable rigid attachment mechanism that enables attachment of an endoscope with the adapter to an instrument. For example, the adapter may utilize a magnetic attachment mechanism, a snap on attachment mechanism, a top-down ratchet mechanism, an insert ratchet mechanism, and/or an insert twist mechanism as further described in U.S. Pat. No. 10,512,391, incorporated herein by reference in its entirety. It should be noted that the disclosure is not limited to the specific attachment mechanisms described and illustrated herein, and that other mechanisms for removably coupling the flexible-rigid endoscope to an instrument are contemplated.

As depicted by FIGS. 1B-1C, a rotatable joint 120 positioned between rigid attachment segment 130 and coupler 110 enables rotation of adapter 100 about its longitudinal axis (e.g., rotation of rigid attachment segment 130 relative to coupler 110). In this manner, an endoscope may be removably coupled to an instrument via rigid attachment segment 130 in a plurality of different circumferential positions. Additionally, after coupling, the instrument may be rotated relative to the endoscope, allowing adjustment of the endoscopic image. Rotatable joint 120 may be configured to rotate continuously through 360 degrees or in stepwise degree increments. For example, depending on the desired number possible circumferential positional adjustments, it may be configured to rotate in stepwise increments of 10°, 15°, 20°, 30°, 40°, 45°, 60°, 72°, 90°, 120°, or 180°.

In this example, a coupler 110 is secured to an endoscope housing using a twist on male/female attachment mechanism. A locking screw 140 is used to secure the female coupler 110 to the male coupler of the endoscope (e.g., FIG. 5A, 520; FIG. 8A 810) of the endoscope housing. For example, the locking screw 140 may engage a groove 820 in a male coupler 810. A rotatable, circular joint 120 is fused to the rigid attachment segment 130. The rotatable joint engages the coupler 110 by a circular extension 144 of the rigid attachment segment 130 and connector channel 175 which passes through its center. A small circumferential lip 145 on the proximal end of the circular extension 144 engages a wider circumferential lip 146 within the distal opening of the coupler housing in a manner that allows rotation movement of the joint. The circular, rotatable joint 120 contains a series of small round apertures 143 arranged on the periphery of its inner surface. The angular position of the rotatable joint is secured by a small block 142 pressed into an aperture 143 by a spring 141 contained within a channel 147 located within the coupler housing 110. When the coupler is secured to an endoscope, forceful rotation the attachment segment relative to the coupler causes the block to compress the spring as the block moves out of its occupied aperture. As the rotation continues, the compressed spring pushes the block into the next aperture thereby securing its new position.

Figure 2A:
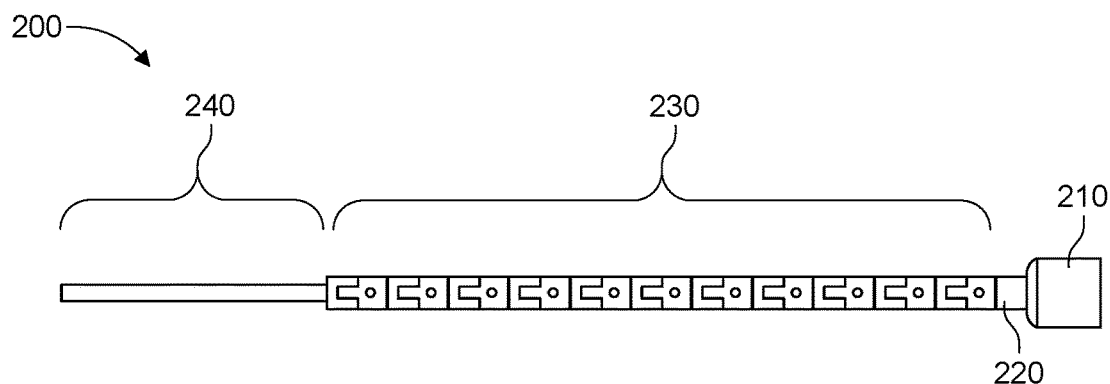
FIG. 2A illustrates a side view of another endoscope attachment adapter, in accordance with some implementations of the disclosure.
Figure 2B:
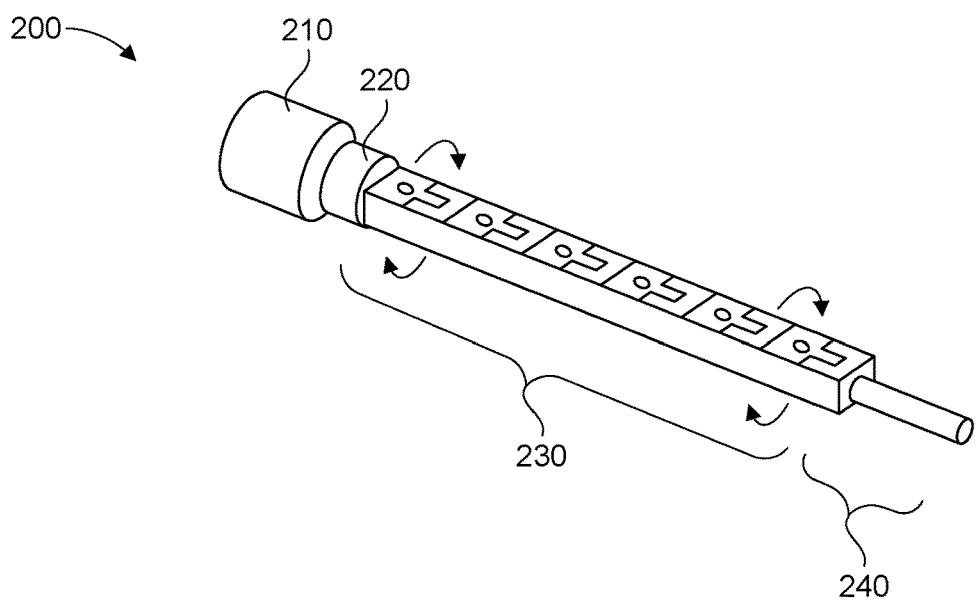
FIG. 2B shows a perspective view of the endoscope attachment adapter of FIG. 2A.

FIGS. 2A-2B illustrate another example endoscope attachment adapter 200, in accordance with implementations of the disclosure. FIG. 2A illustrates a side view of adapter 200, FIG. 2B illustrates a perspective view of adapter 200. Adapter 200 includes a stationary coupler 210, a rotatable joint 220, a rigid attachment segment 230, and a distal segment 240. The distal segment 240 may vary in length and may be rigid or flexible. In this example, the inclusion of additional distal segment 240 may help further stabilize the endoscope and attachment adapter after it is coupled to an endoscope (e.g., by threading the endoscope through a channel running through coupler 210, joint 220, rigid attachment segment 230, and distal segment 240). This may be particularly advantageous when threading the adapter over a flexible endoscope. For example, by changing the length of the distal segment 240 and rigid attachment segment 230, a flexible endoscope can be converted into a rigid endoscope or hybrid endoscope with varying lengths of rigid or flexible segments. In some implementations, the distal segment 240 may incorporate a circular indentation or other means by which other sleeve adapters more distal to itself can be secured. Such other adapters may include, but are not limited to flexible or rigid sleeve adapters that contain suction/irrigation capabilities and/or sleeve adapters that have an attached channel, tube, magnet, clip(s), suction cup(s), "zip-lock" mechanism, or other mechanism of securing the distal end of the endoscope and sleeve adapter to an instrument shaft or device.

Figure 3A:
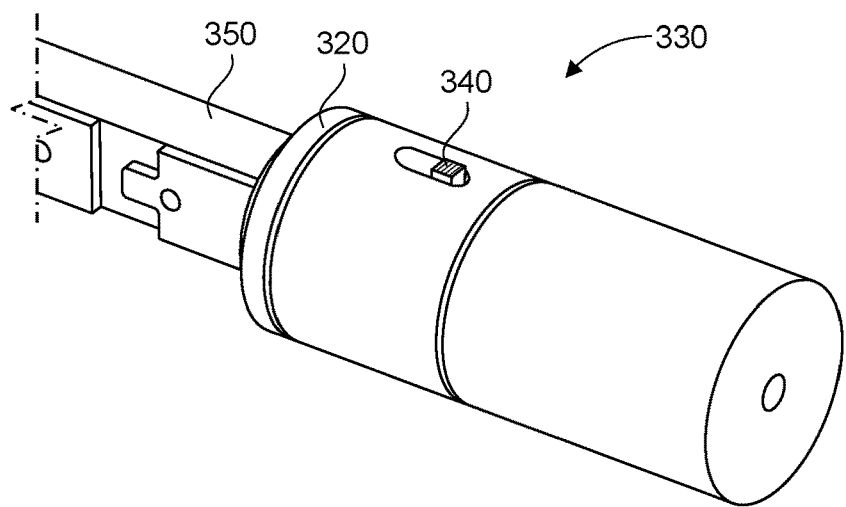
FIG. 3A shows the proximal part of an endoscope attachment coupler, in accordance with some implementations of the disclosure.
Figure 3B:
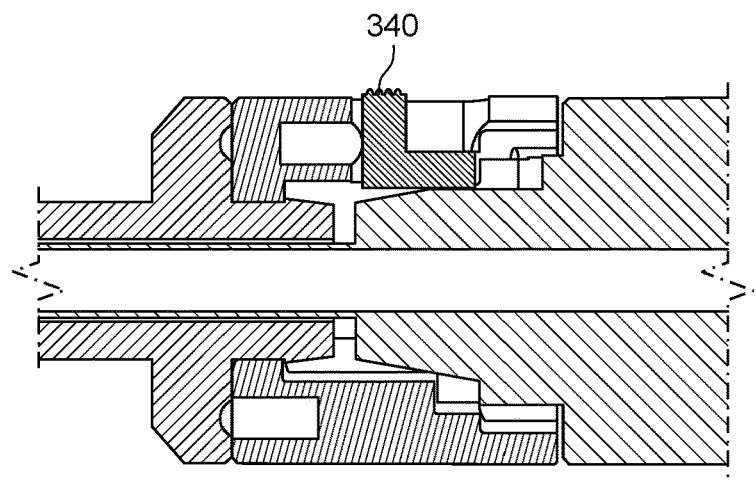
FIG. 3B shows a cross-sectional view of the locking mechanism of the coupler of FIG. 3A, in accordance with some implementations of the disclosure.
Figure 3C:
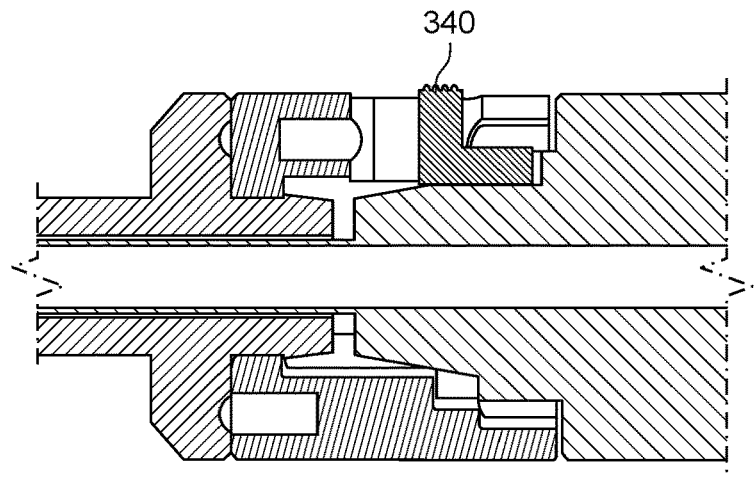
FIG. 3C shows a cross-sectional view of the locking mechanism of the coupler of FIG. 3A, in accordance with some implementations of the disclosure.

FIGS. 3A-3C illustrate the proximal part of another example endoscope attachment coupler 330, in accordance with implementations of the disclosure. In this example, the attachment coupler 330 may be a female coupler that twists onto a male coupler 810 of an endoscope housing 310 and is locked in place by a slidable control 340 that functions similar to the locking screw 140 shown in FIGS. 1B-1D. The attachment coupler 330 includes a rotatable joint 320 that enables rotation of rigid attachment adapter 350 about its longitudinal axis, in a manner previously described. FIGS. 3B-3C depict a cross-sectional view showing a locking mechanism of coupler 330 that includes a slidable control 340 (e.g., embedded in the proximal part of coupler 330) that locks the attachment coupler 330 to the endoscope housing 310 by sliding into a groove 820 along the top edge of the male endoscope coupler 810. FIG. 3B shows the locking mechanism in an unlocked position. FIG. 3C shows the locking mechanism in a locked position.

Figure 4A:
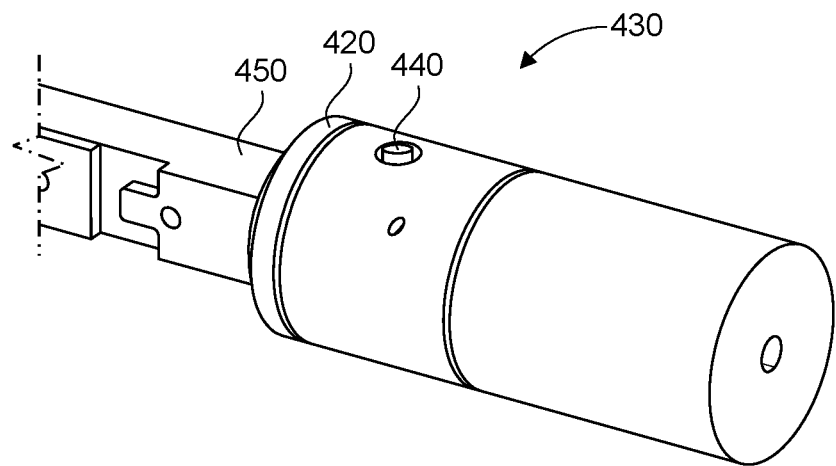
FIG. 4A shows the proximal part of another endoscope attachment coupler, in accordance with some implementations of the disclosure.
Figure 4B:
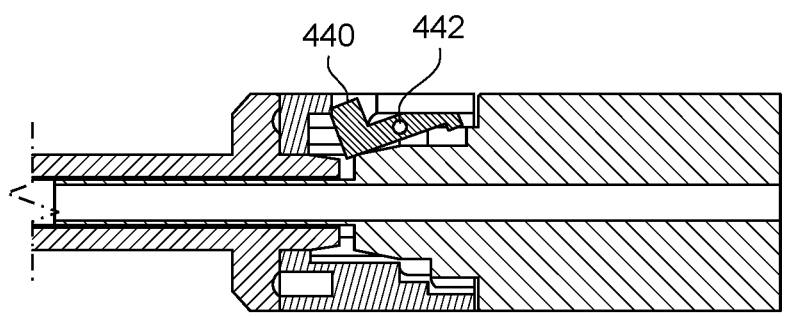
FIG. 4B shows a cross-sectional view of the locking mechanism of the coupler of FIG. 4A, in accordance with some implementations of the disclosure.

FIGS. 4A-4B illustrate a proximal part of another example endoscope attachment coupler 430, in accordance with implementations of the disclosure. In this example, the proximal aspect of the attachment coupler 430 may twist onto the male coupler 810 of an endoscope housing 410 and be locked into position by a lever 442 actuated (released) by a depressible button 440. The attachment coupler 430 includes a rotatable joint 420 that enables rotation of rigid attachment adapter 450 about its longitudinal axis, in a manner previously described. A depressible button 440 attaches to a lever arm 442 that may engage a groove 820 along the top edge of the male endoscope coupler 810. FIG. 4B depicts a cross-sectional view showing a locking mechanism of coupler 430 that locks rotatable joint 420 in place. FIG. 4B shows the locking mechanism in the unlocked position.

As should be appreciated from the foregoing examples, the adapter may use any suitable mechanism (e.g., screw, slidable control, pressable control, magnetic, twist on spring tension, etc.) that may be actuated to lock the adapter onto the endoscope housing.

Figure 5A:
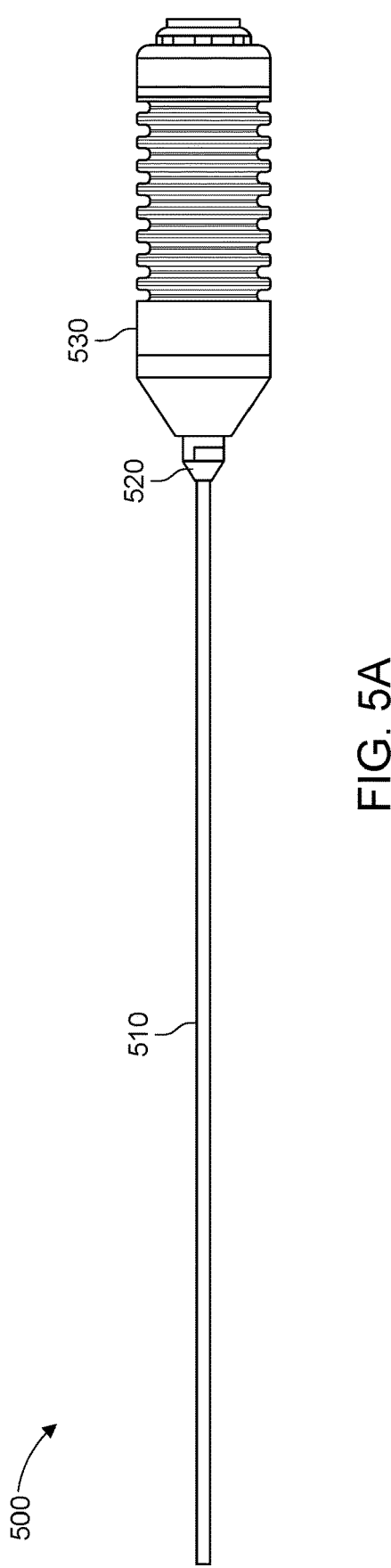
FIG. 5A shows an endoscope to which an endoscope adapter may be coupled to, with the endoscope adapter not coupled, in accordance with some implementations of the disclosure.
Figure 5B:
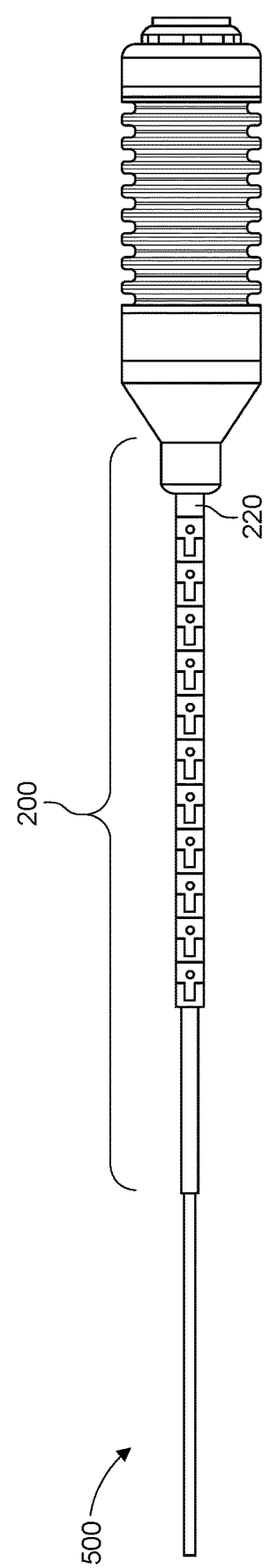
FIG. 5B shows the endoscope of FIG. 5A with the endoscope adapter coupled to the endoscope.

FIGS. 5A-5B depict an endoscope 500 to which an endoscope adapter may be coupled to, in accordance with implementations of the disclosure. The endoscope 500 includes a shaft 510, a connector 520 adjacent a proximal end of shaft 510, and an endoscope head and/or handle 530 adjacent the connector 520. Shaft 510 may rigid, flexible (e.g., bendable), removable, disposable, or it may be part rigid, flexible, or malleable (hybrid). As shown in FIG. 5B, shaft 510 may be threaded through a channel of an adapter 200 and connector 210 of adapter 200 may be secured to connector 520 of endoscope 500. Although adapter 200 is shown removably coupled to the endoscope 500 in FIG. 5B, it should be appreciated that any of aforementioned adapters (e.g., 100, 200, etc.) may be removably coupled to the endoscope 500. It should be further appreciated that any of the aforementioned adapters may either include a rotatable joint or instead be attached to the endoscope in a fixed manner incapable of manual rotation along its longitudinal axis.

In some embodiments, the endoscope shaft (flexible, rigid, or hybrid) may in and of itself be detachable and re-attachable from the endoscope head or rigid attachment segment. Such removable shafts may be capable of receiving an adapter coupler or may instead already have an adapter configuration 200 as part of their shaft structure. Detachable shaft configurations of different sizes, shapes, profiles, rigidity, and attachment segment lengths with instrument attachment capabilities would permit single use, disposable sterilized shafts and custom configurations for instrument attachment depending on the surgical application.

Once adapter 200 is secured to endoscope 500 (e.g., as depicted in FIG. 5B), endoscope 500 may be removably coupled to a channel of an instrument (further discussed below), in a plurality of different lengthwise positions via rigid attachment segment 230, and/or a plurality of different circumferential positions via rotatable joint 220. Although in this example adapter 200 includes a rotatable joint for manually rotating the endoscope for image orientation and/or positioning, alternative implementations described below describe an adapter without a rotatable joint that may instead rely on digital image rotation.

Figure 6:
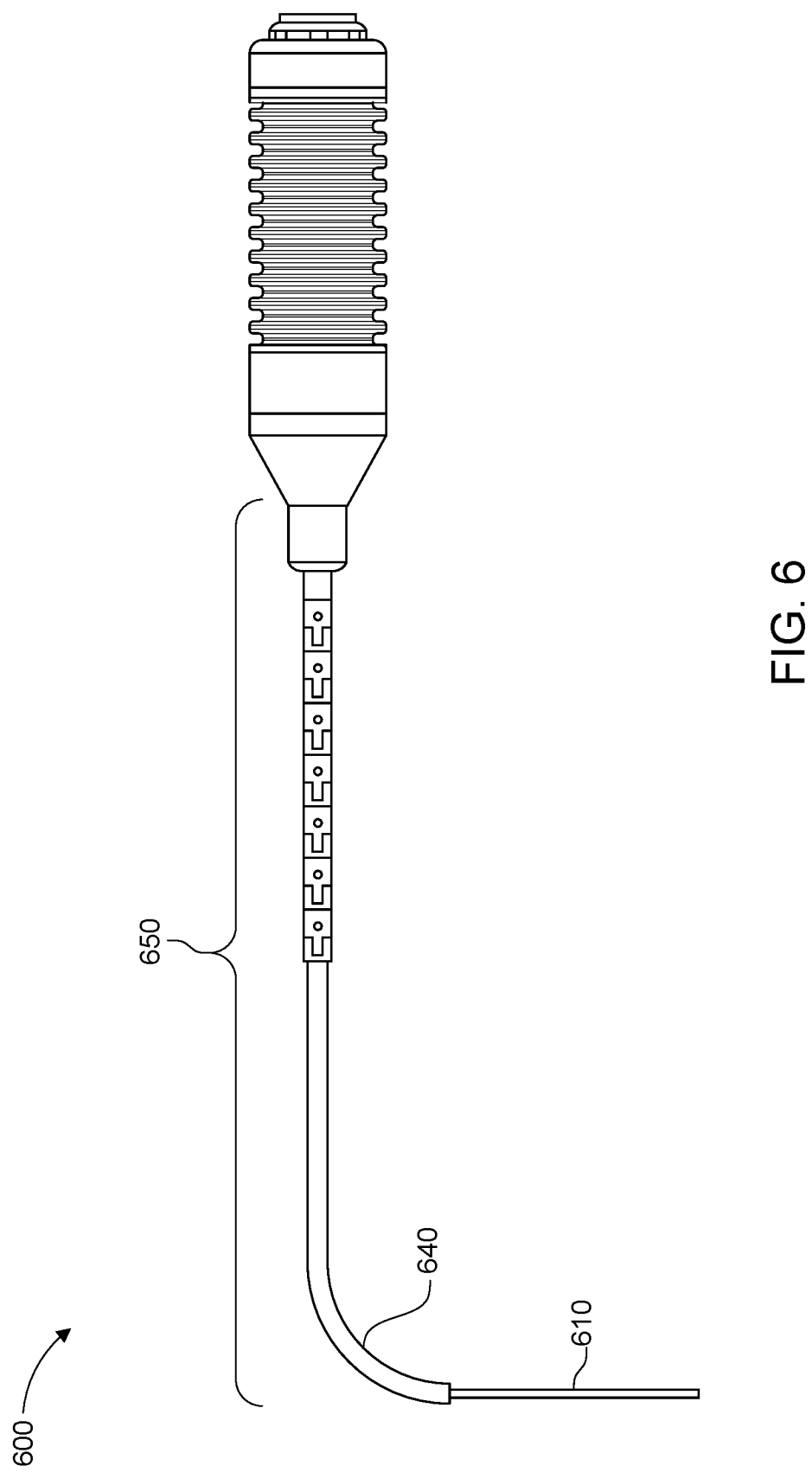
FIG. 6 shows an endoscope attachment adapter removably coupled to an endoscope with a flexible shaft, in accordance with some implementations of the disclosure.
Figure 7:
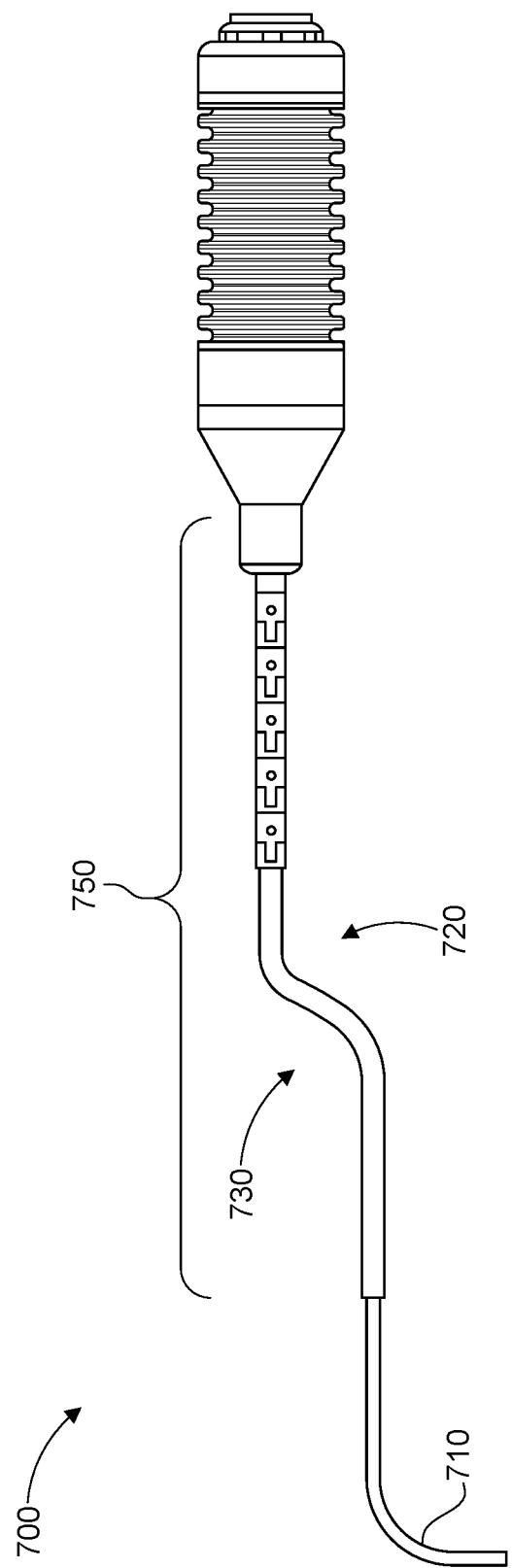
FIG. 7 shows an endoscope attachment adapter removably coupled to another endoscope with a flexible shaft, in accordance with some implementations of the disclosure.

FIG. 6 depicts an endoscope attachment adapter 650 removably coupled to an endoscope 600 with a flexible shaft 610. In this example, an angled distal part 640 of the adapter 650 causes the endoscope shaft 610 to bend 90 degrees after the adapter 650 is coupled to the endoscope. FIG. 7 depicts an endoscope attachment adapter 750 removably coupled to another endoscope 700 with a flexible shaft 710. This adapter causes the endoscope shaft to take on multiple bends, 720, 730. In these examples, threading the flexible scope through a rigid or semi-rigid adapter with a single bend (adapter 650) or multiple bends (adapter 750) may be difficult. For this reason, the distal segments of the rigid sleeve adapters (650, 750) may require relief slots along the radius of the bends to facilitate the threading of the scope through the adapter.

FIG. 8A shows an endoscope 800 with a twist-on male coupler 810 attached to the endoscope head 830. The coupler has a small groove or slot 820 that engages the locking mechanisms, previously described for the attached adapters. FIG. 8B shows an endoscope 850 that contains a rotatable ring 860 on the proximal part of the endoscope housing 870. The endoscope shaft 855 of endoscope 850 includes a non-rotatable adapter on the proximal part of endoscope shaft 855 that is coupled in a non-rotatable manner to the endoscope housing 870. The rotatable ring 860 may be used to digitally adjust an orientation of captured video/images in real time. Techniques for digitally adjusting the orientation of the captured endoscope video/images in real time are further described in U.S. patent application Ser. No. 16/664,723, incorporated herein by reference. By virtue of this endoscope configuration, an attachment adapter with a rotatable joint may not be needed to operate the endoscope and capture/observe images at different orientations. This does not preclude, however, endoscopes of this type receiving couplers with a rotatable joint.

Figure 9:
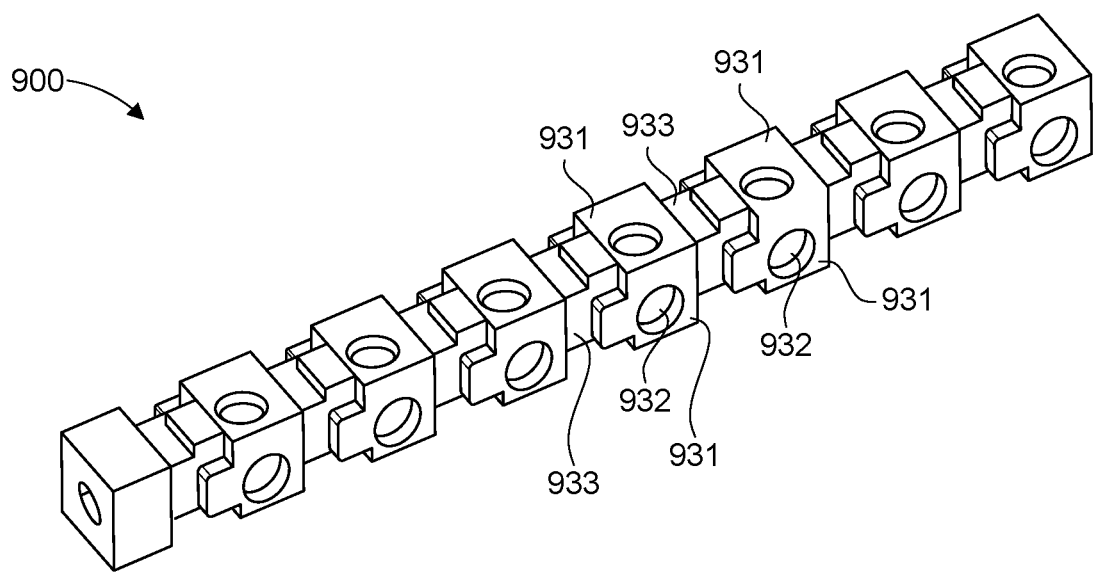
FIG. 9 shows a fixed endoscope attachment adapter, in accordance with some implementations of the disclosure.

As noted above, in some implementations, the endoscope attachment adapter may be configured to be fixed in place as opposed to being capable of rotating about its longitudinal axis. In such instances, the adapter may not include a rotatable joint (e.g., rotatable joint 120). FIG. 9 depicts one such example of a fixed endoscope attachment adapter 900. In adapter 900, the rigid attachment segment is four-sided with a square cross section. In contrast to rigid attachment segment 130, the attachment mechanism is formed on multiple sides (e.g., two, three, or all four) of the rigid attachment segment of adapter 900. That is, multiple grooves 933 and multiple sections 931, each of the sections 931 having a recessed indentation or hole 932, are formed on each of the multiple sides of the rigid attachment segment. As such, even though adapter 900 is not rotatable about a rotatable joint, it may still be used to couple an endoscope to an instrument channel in multiple circumferential positions by virtue of having the attachment segment formed on the rigid attachment segment.

Figure 10:
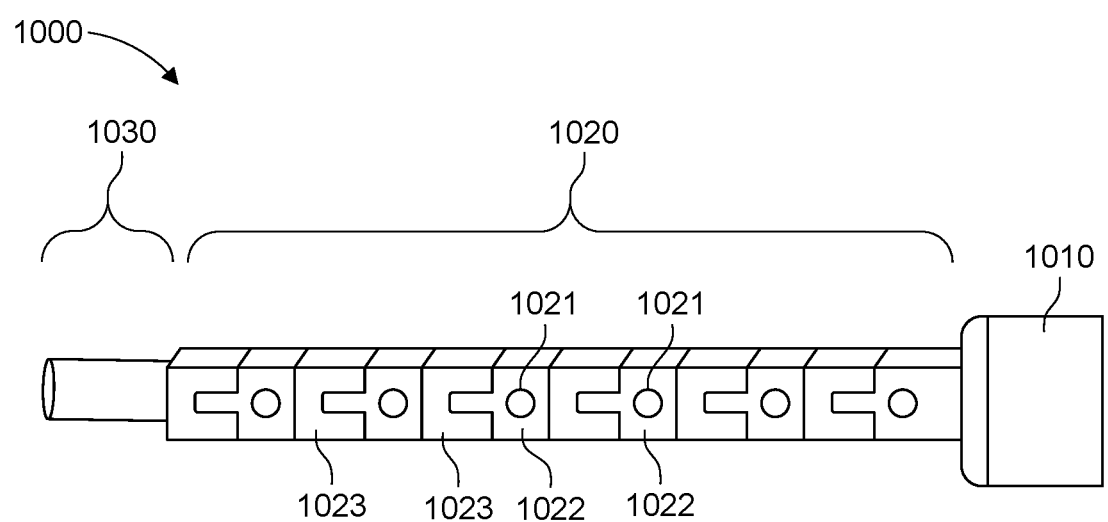
FIG. 10 shows another fixed endoscope attachment adapter, in accordance with some implementations of the disclosure.

FIG. 10 depicts another example of a fixed endoscope attachment adapter 1000. As depicted, adapter 1000 includes a connector 1010, rigid attachment segment 1020, and distal segment 1030. In some implementations, distal segment 1030 may be omitted. In adapter 1000, rigid attachment segment 1020 is four-sided with a square cross section. In contrast to rigid attachment segment 1030, the attachment mechanism is formed on multiple sides (e.g., two, three, or all four) of rigid attachment segment 1020. That is, multiple grooves 1023 and multiple sections 1022, each of the sections 1022 having a recessed indentation or hole 1021, are formed on each of the multiple sides of segment 1020. Section 1030 may in some instances be configured to receive adapter sleeves for implementing attachment of the distal scope shaft to an instrument, permitting suction/irrigation for cleaning the endoscope tip, providing a conduit for electrical current to be delivered to the scope or instrument tip, etc.

Figure 11A:
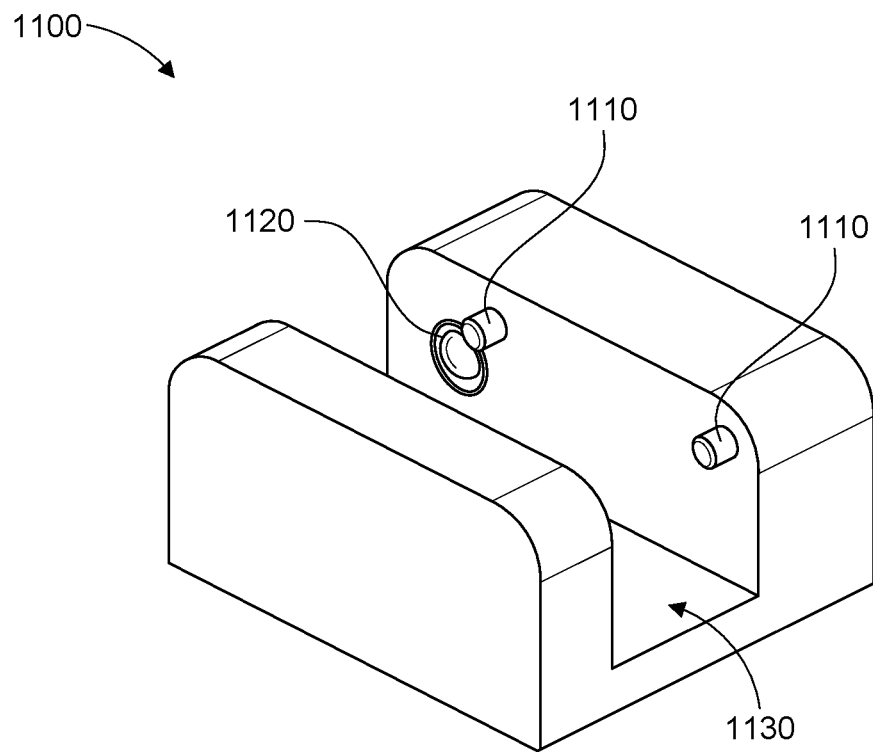
FIG. 11A shows an instrument housing that an endoscope attachment adapter may be removably coupled to, in accordance with some implementations of the disclosure.

FIG. 11A depicts an instrument housing 1100 that an endoscope attachment adapter (e.g., adapter 100) may be removably coupled to, in accordance with implementations of the disclosure. The instrument housing 1100 may be integrated near the top, on the side (e.g., FIG. 15 A-C), or underneath the handle portion of an instrument or instrument shaft. For example, the instrument housing 1100 may be part of a handle of an instrument such as a bipolar suction cautery, coblation wand, laryngeal forceps, sinus forceps, orthopedic articulating forceps, a laryngeal syringe gun, an endoscopic Eustachian tube balloon dilator, an endoscopic tracheal dilator, an endoscopic trans-oral esophageal balloon dilator, injection syringe, or some other instrument. Housing 1100 utilizes a top-loading ratchet mechanism to secure an adapter 100 to the instrument. As such, an endoscope with a coupled adapter 100 may be removably coupled in a top-down manner by pushing down the proximal end of the endoscope shaft with the adapter (i.e., pushing down rigid attachment segment 130) into an open channel 1130 of housing 1100.

Figure 11B:
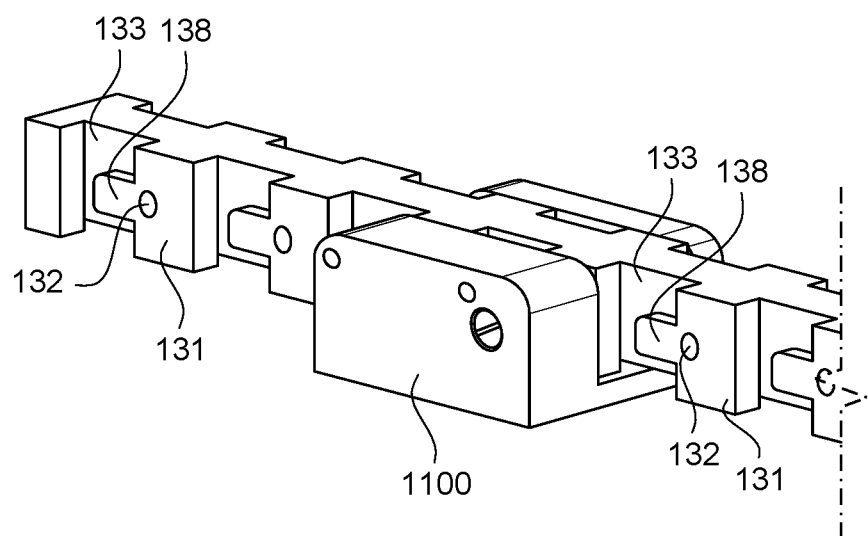
FIG. 11B shows the instrument housing of FIG. 11A removably coupled to a rigid attachment segment of an adapter, in accordance with some implementations of the disclosure.
Figure 12A:
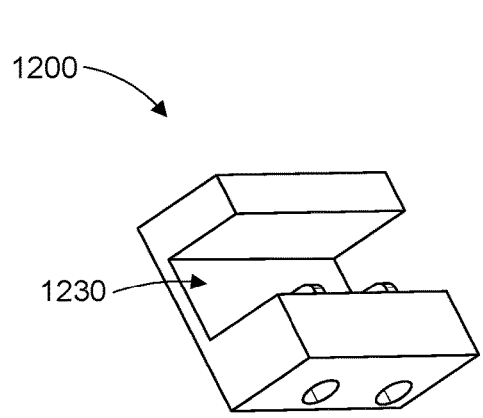
FIG. 12A shows a perspective view of another instrument housing that an endoscope attachment adapter may be removably coupled to, in accordance with some implementations of the disclosure.
Figure 12B:
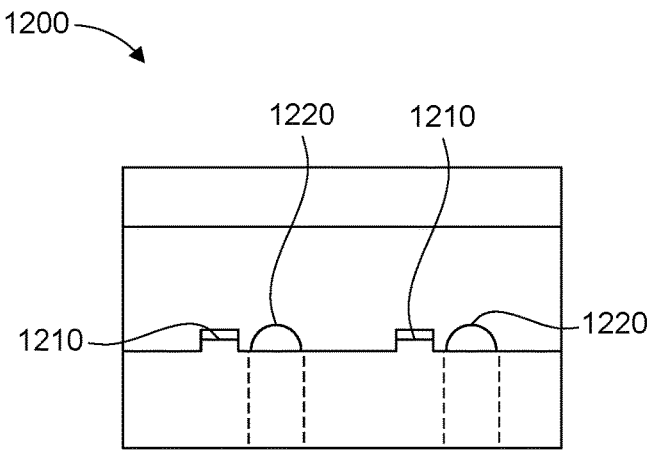
FIG. 12B shows a cross-sectional view of the instrument housing of FIG. 12A.
Figure 12C:
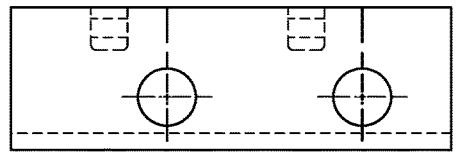
FIG. 12C shows another cross-sectional view of the instrument housing of FIG. 12A.
Figure 12D:
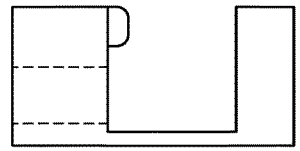
FIG. 12D shows a side view of the instrument housing of FIG. 12A.

As depicted, the interior surface of housing 1100 includes an open channel 1130, ridges, pins, or protrusions 1110, and spring-loaded protrusion (e.g., spring-loaded ball) 1120. Rigid attachment segment 130 may be secured in place by i) pushing it down into open channel 1130 along openings of two adjacent grooves 133; and ii) sliding rigid attachment segment 130 relative to open channel 1100 to position each ridge 1110 within a respective groove 133 of the adjacent grooves 133 such that protruding portions 138 of sections 131 adjacent the grooves 133 prevent lifting of the rigid attachment segment 130 (i.e., they block ridges 1110). Additionally, when the assembly is slid, spring-loaded protrusion 1120 may be secured within an indentation/hole 132 of the section 131 positioned between the two grooves 133. To reposition rigid attachment segment 130 at a different lengthwise position, the above-described operations may be reversed (i.e., it may be slid out of place, lifted off, and secured along other grooves 133). By way of illustration, FIG. 11B shows a housing 1100 removably coupled to a rigid attachment segment 130 of an adapter 100. In alternative implementations, the positions of spring-loaded protrusion 1120 and indentation/hole 132 may be reversed, i.e., the indentation 132 is part of the housing 1100 and the spring-loaded protrusion is part of the adapter 100.

By virtue of utilizing this attachment mechanism, the endoscope may be quickly secured within the instrument housing 1100 at a particular lengthwise position without the requirement of an elongated open channel 1130. This type of attachment mechanism may eliminate any rocking of the endoscope shaft within the open channel 1100 and allow for shorting of the open channel when compared to the depressible button/lever mechanism previously described in U.S. Pat. No. 10,512,391. Additionally, the top-loading ratchet mechanism described herein provides a quick and simple means for securing an endoscope to an instrument. Coupling, uncoupling, and/or repositioning an endoscope within the instrument is simply a matter of lifting down/up and sliding such that ridges 1110 are inserted into a particular set of grooves 133 and spring-loaded protrusion 1120 is secured within a particular indentation 1132.

FIGS. 12A-12D illustrate another example of an instrument housing 1200 that an endoscope attachment adapter (e.g., adapter 100) may be removably coupled to, in accordance with implementations of the disclosure. In this implementation, the interior surface of housing 1200 includes an open channel 1230, ridges or protrusions 1210, and, in this instance, multiple spring-loaded protrusions (e.g., spring-loaded balls) 1220. Rigid attachment segment 130 may be secured in place by i) pushing it down into open channel 1230 along openings of two adjacent grooves 133; and ii) sliding rigid attachment segment 130 relative to open channel 1230 to position each ridge 1210 within a respective groove 133 of the adjacent grooves 133 such that protruding portions 138 of sections 131 adjacent the grooves 133 prevent lifting of the rigid proximal attachment segment 130 (i.e., they block ridges 1210). Additionally, when the assembly is slid, spring-loaded protrusions 1220 may be secured within an indentation/hole 132 of the sections 131 positioned next to the two grooves 133.

Figure 13A:
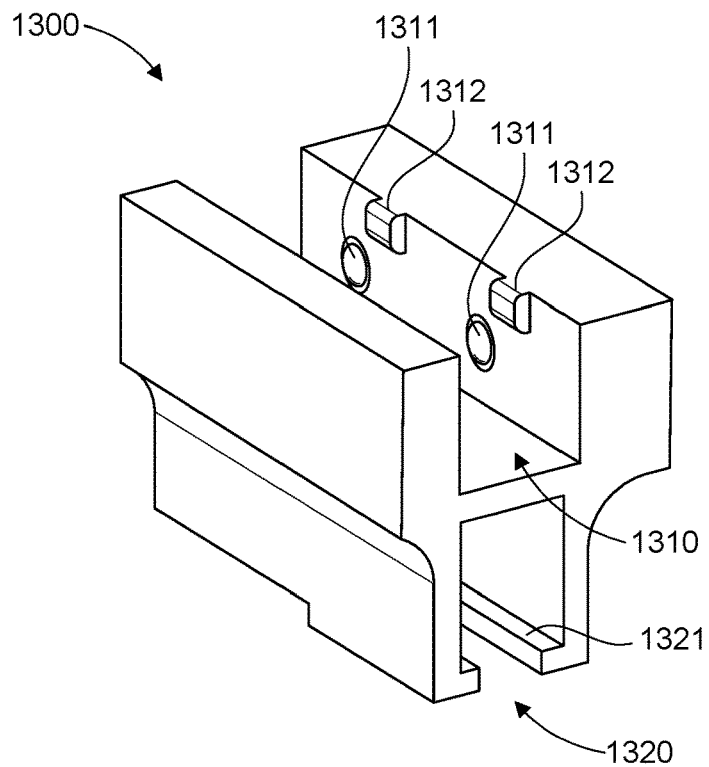
FIG. 13A shows an H-channel adapter that may be removably coupled to the attachment segment of an endoscope shaft, endoscope attachment adapter, and/or endoscope instrument tools, in accordance with some implementations of the disclosure.

FIG. 13A illustrates an H-channel adapter 1300 that may be removably coupled to the attachment segment of an endoscope shaft, endoscope attachment adapter (e.g., adapter 100), and/or endoscope instrument tools, in accordance with implementations of the disclosure. As depicted, H-channel adapter 1300 includes an upper open channel 1310 for removably coupling H-channel adapter 1300 to endoscope attachment adapter 100, and a lower open channel 1320, opposite the upper open channel 1310, for removably coupling H-channel adapter 1300 to endoscope instrument tools.

Figure 13B:
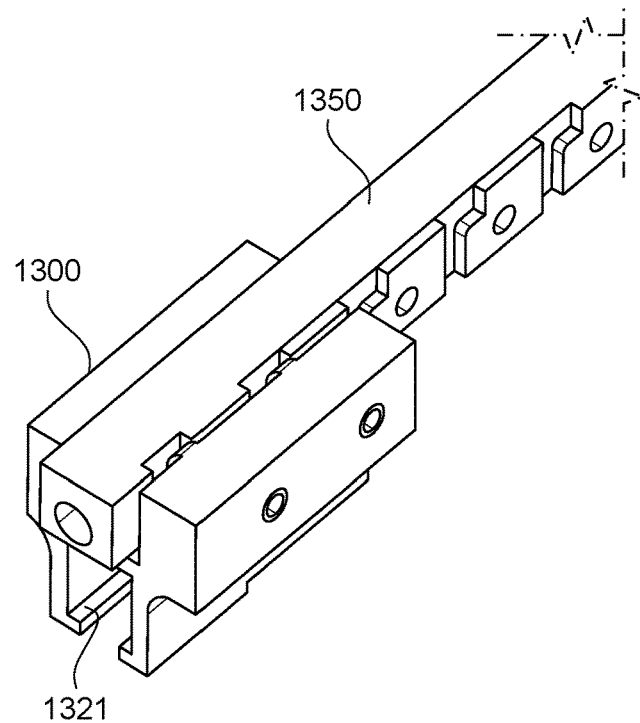
FIG. 13B shows the H-channel adapter of FIG. 13A attached to a distal end of an endoscope attachment adapter.

The interior surface of the upper open channel 1310 includes ridges or protrusions 1312, and spring-loaded protrusions (e.g., spring-loaded balls) 1311. Rigid attachment segment 130 may be secured in place by i) pushing it down into upper open channel 1310 along openings of two adjacent grooves 133; and ii) sliding rigid attachment segment 130 relative to open channel 1310 to position each ridge 1312 within a respective groove 133 of the adjacent grooves 133 such that protruding portions 138 of sections 131 adjacent the grooves 133 prevent lifting of the rigid attachment segment 130 (i.e., they block ridges 1312). Additionally, when the assembly is slid, spring-loaded protrusions 1311 may be secured within an indentation/hole 132 of the sections 131 positioned next to the two grooves 133. In certain semi-rigid or plastic channel and shaft embodiments, a rounded protrusion may suffice instead of a spring loaded protrusion. FIG. 13B depicts an example of H-channel adapter 1300 attached to a distal end of an endoscope attachment adapter 1350.

The interior surface of the lower open channel 1320 includes side rails 1321 for slidably coupling an instrument tool. For example, forceps, suctions, graspers, culture tools, fasteners, staplers, or some other instrument tool contain side grooves or longitudinal slots to engage side rails 1321 allowing attachment to the underside of the endoscope via lower open channel 1320. Although a sliding mechanism is illustrated coupling lower open channel 1320 to an instrument tool, it should be appreciated that any suitable coupling mechanism may be utilized.

By virtue of utilizing the H-channel adapter 1300 that may be removably attached to an endoscope attachment adapter (e.g., adapter 100) in a convenient lengthwise position, instrument tools may be attached in a suitable position underneath the endoscope with the adapter 100 and H-channel adapter 1300. By incorporating several instrument channels offset from one another into the same adapter, multiple instruments could be simultaneously attached to the endoscope at the same time. This would be helpful when performing rigid laryngoscopy when there may be need for a forceps, suction, laser, and endoscope all working together at the same time through a single rigid tube.

In other embodiments, other adapters may be used that have two or more channels that are offset 90 degrees from one another in an either side by side, or otherwise offset manner.

Figure 14A:
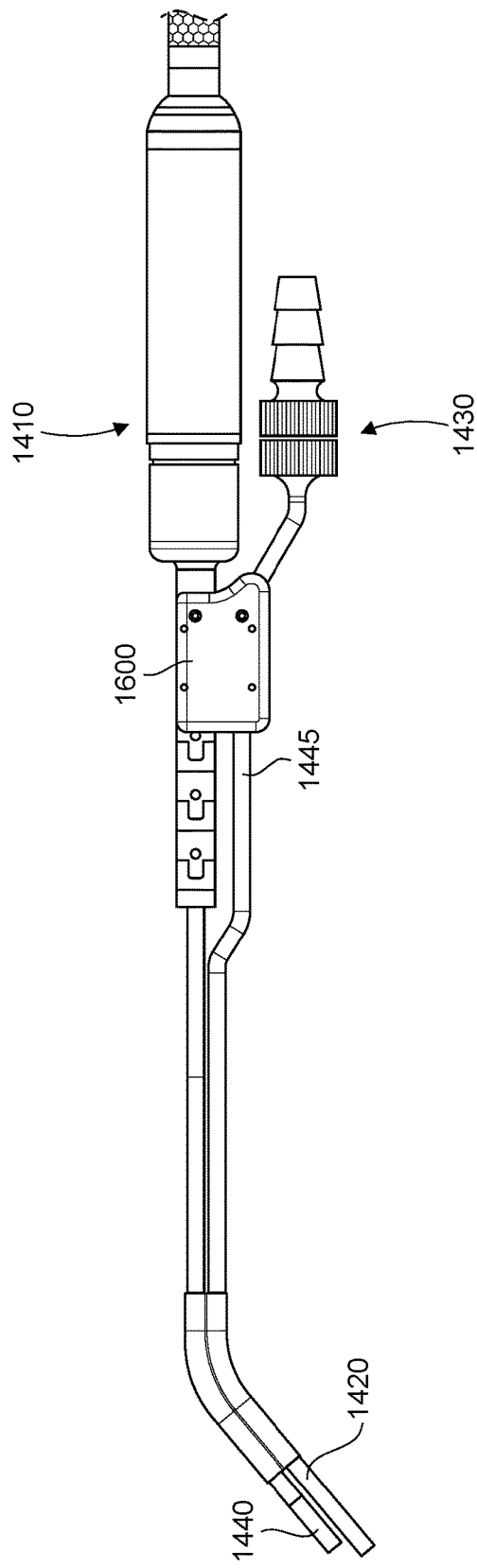
FIG. 14A shows an endoscope coupled to an instrument via an H-channel adapter, in accordance with some implementations of the disclosure.

FIG. 14A depicts an endoscope 1410 coupled to an instrument 1430 via an H-channel adapter 1600 in accordance with implementations of the disclosure. The distal shaft 1420 of the instrument 1430 is shown to extend underneath the endoscope shaft 1440. The proximal shaft 1445 of instrument 1430 connects to endoscope 1410 via H-channel adapter 1600 and a rigid attachment segment on the shaft of the endoscope (e.g., rigid attachment segment 130 of adapter 100) as discussed above. The rigid attachment segment may be part of an adapter (e.g., adapter 100) that couples to a proximal part of the shaft of the endoscope 1410 or integrated into a proximal part of the shaft of the endoscope 1410.

Figure 14B:
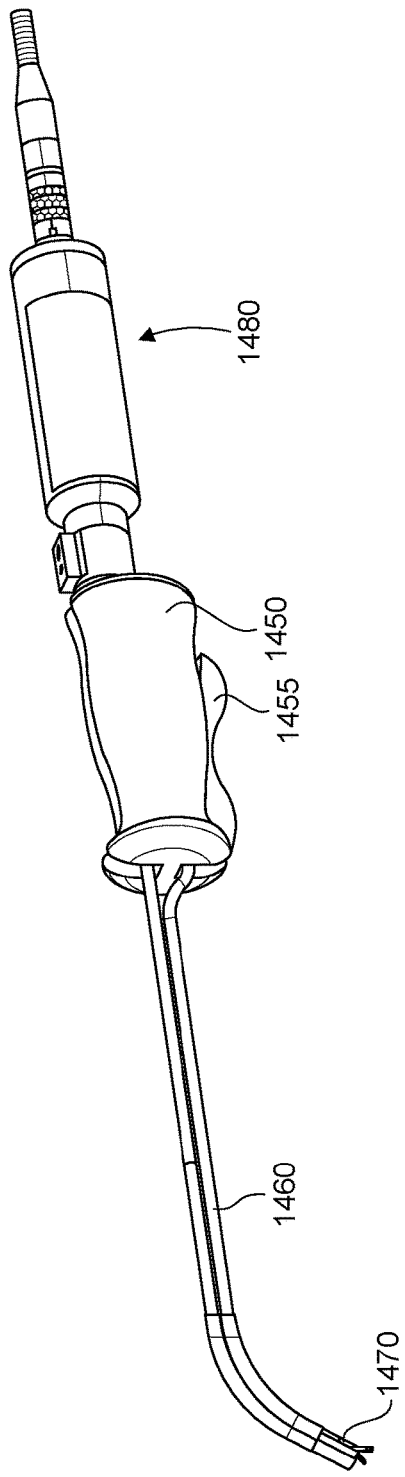
FIG. 14B shows an endoscope coupled to an instrument and instrument shaft, in accordance with some implementations of the disclosure.

FIG. 14B depicts an endoscope 1480 coupled to an instrument 1450 and instrument shaft 1460 in accordance with implementations of the disclosure. A top portion of instrument 1450 includes an open channel that couples to endoscope 1410 via a rigid attachment segment on the shaft of the endoscope (e.g., rigid attachment segment 130 of adapter 100) as discussed above. The rigid attachment segment may be part of an adapter (e.g., adapter 100) that couples to a proximal part of the shaft of the endoscope 1480 or integrated into a proximal part of the shaft of the endoscope 1480. In this embodiment, instrument 1450 includes a handle mechanism 1455 to actuate tool tip 1470 attached to instrument shaft 1460. In this manner the instrument and scope are connected and the tool is actuated in a linear, streamlined manner (hand over top of the instrument instead of underneath) avoiding the need for a larger handle angled away from the scope. Additionally, this implementation has the advantage of not requiring a separate H-channel adapter. Rather, the upper channel for coupling to the endoscope is integrated into the instrument 1450.

Figure 15A:
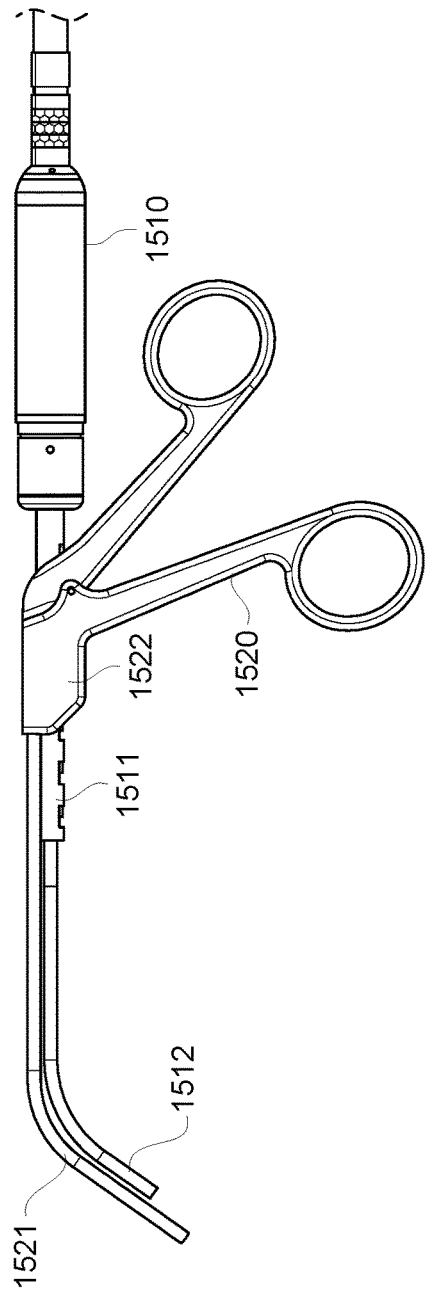
FIG. 15A shows a side view of an assembly including a forceps instrument removably coupled to an endoscope via an endoscope attachment adapter, in accordance with some implementations of the disclosure
Figure 15B:
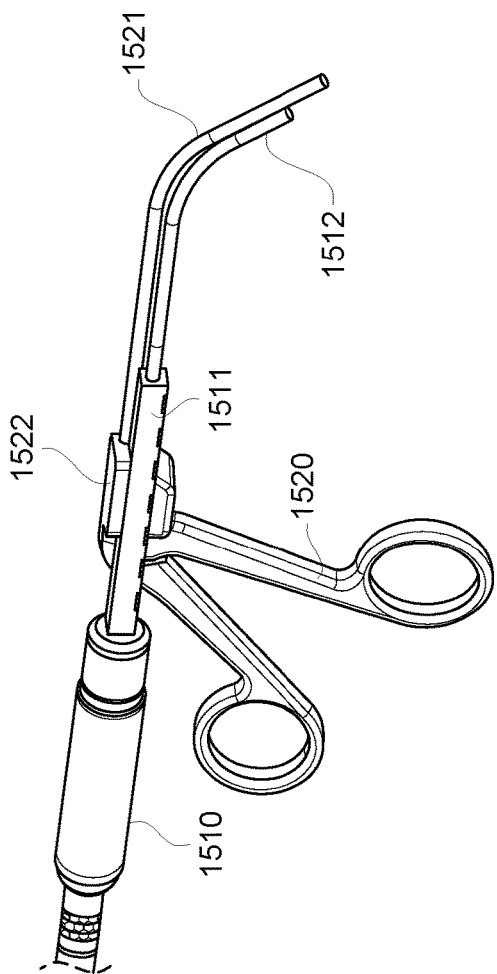
FIG. 15B shows a perspective view of the assembly of FIG. 15A.
Figure 15C:
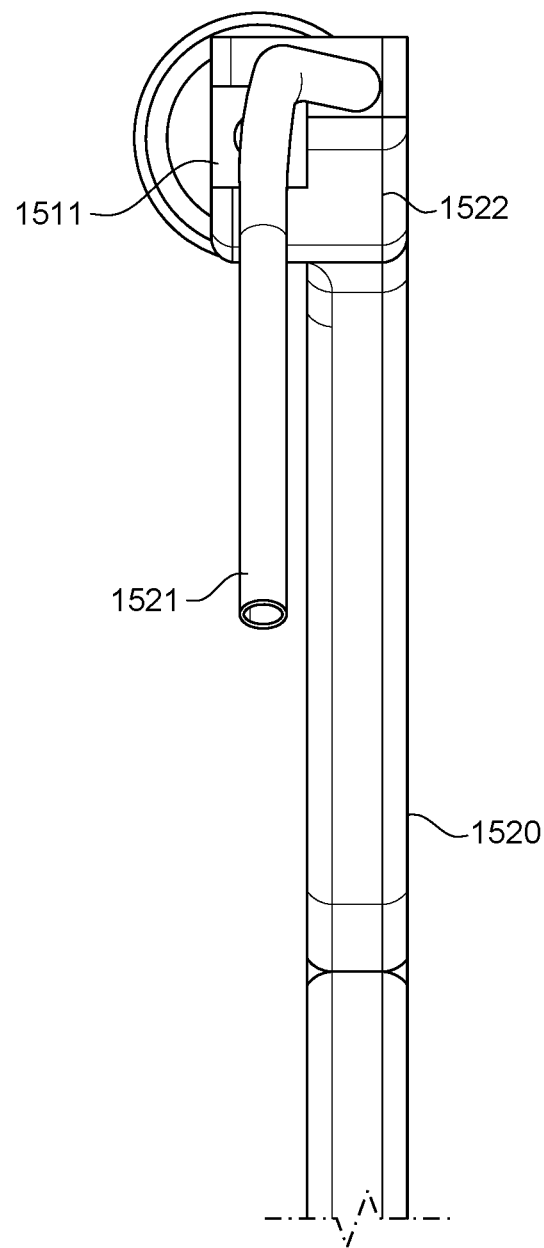
FIG. 15C shows a frontal view of the assembly of FIG. 15A.

FIGS. 15A-15C depict an assembly including a forceps instrument 1520 removably coupled to an endoscope 1510 via an endoscope attachment adapter 1511, in accordance with implementations of the disclosure. FIG. 15A depicts a side view of the assembly, FIG. 15B depicts a perspective view of the assembly, and FIG. 15C depicts a frontal view of the assembly. After threading it through a shaft of endoscope 1510, the endoscope attachment adapter 1511 may be secured at a proximal end of the shaft of endoscope 1510. The forceps instrument 1520 includes a handle, including an integrated instrument housing 1522 that endoscope attachment adapter 1511 is removably coupled to, and a distal tool portion 1521. As depicted in this embodiment, the instrument housing channel 1522 is oriented to the side rather than on the top of the instrument 1520. The endoscope attachment adapter 1511 and the instrument housing 1522 may be structured in a manner similar to that previously described above. By virtue of using the endoscope attachment adapter 1511, a distal portion 1512 of endoscope 1510 may be conveniently positioned underneath and adjacent to tool portion 1521 of forceps instrument 1520 to capture a suitable image of a patient's cavity.

Figure 16A:
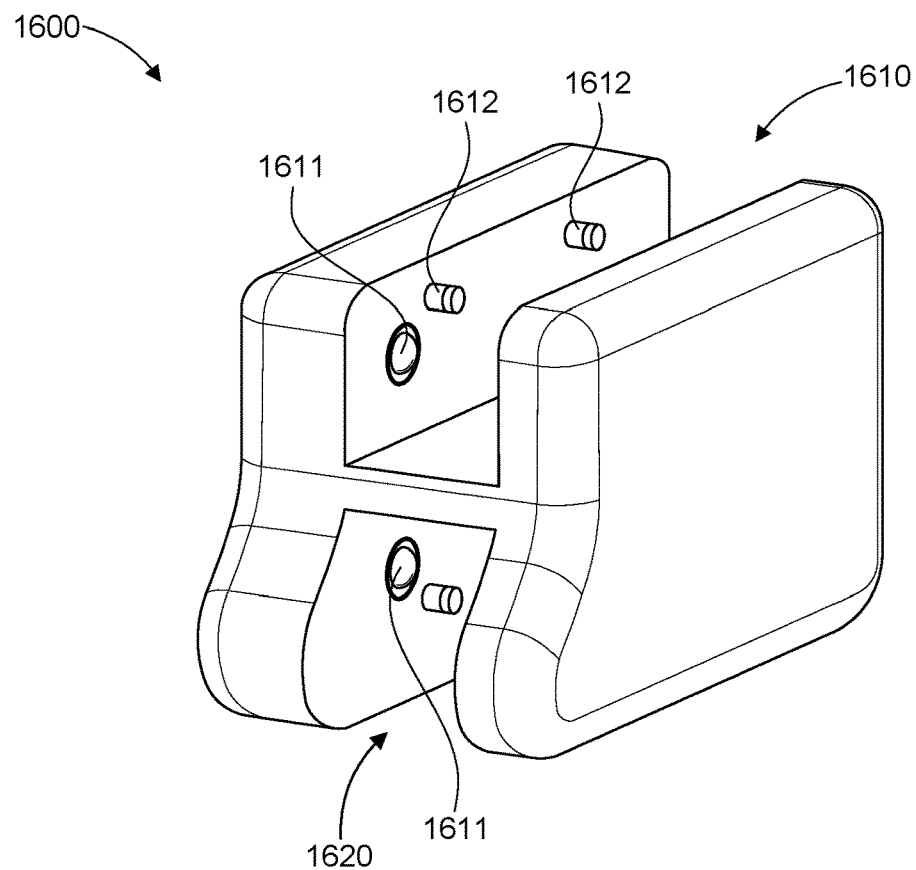
FIG. 16A shows a perspective view of an H-channel adapter that may be removably coupled to an endoscope attachment adapter and endoscope instrument tools, in accordance with some implementations of the disclosure.
Figure 16B:
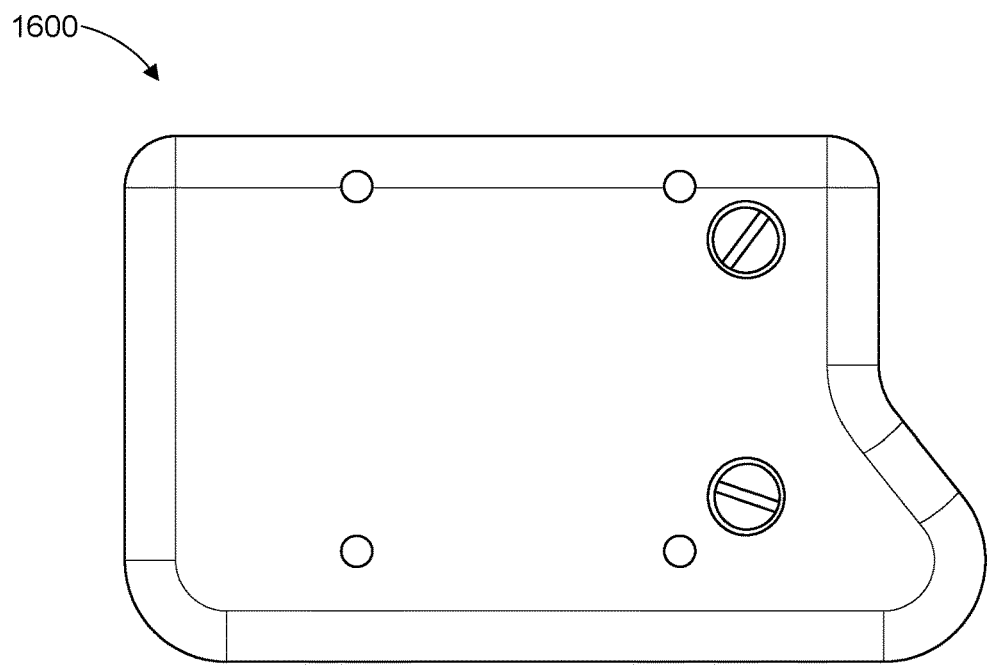
FIG. 16B shows a side view of the H-channel adapter of FIG. 16A.

FIGS. 16A-16B illustrates an H-channel adapter 1600 that may be removably coupled to an endoscope attachment adapter (e.g., adapter 100) and endoscope instrument tools, in accordance with implementations of the disclosure. As depicted, H-channel adapter 1600 includes an upper open channel 1610 for removably coupling H-channel adapter 1600 to an endoscope attachment adapter or to an instrument, and a lower open channel 1620, opposite the upper open channel 1610, for removably coupling H-channel adapter 1600 to an endoscope attachment adapter or to an instrument. In alternative implementations, there may be three or more channels integrated into the same adapter offset from one another at different angles. Such implementations would allow multiple instruments and/or endoscopes to be attached together at the same time.

The interior surface of the upper open channel 1610 includes ridges or protrusions 1612, and a spring-loaded protrusion (e.g., spring-loaded ball) 1611. Rigid attachment segment 130 may be secured in place by i) pushing it down into upper open channel 1610 along openings of two adjacent grooves 133; and ii) sliding rigid attachment segment 130 relative to open channel 1610 to position each ridge 1612 within a respective groove 133 of the adjacent grooves 133 such that protruding portions 138 of sections 131 adjacent the grooves 133 prevent lifting of the rigid attachment segment 130 (i.e., they block ridges 1612). Additionally, when the assembly is slid, spring-loaded protrusion 1611 may be secured within an indentation/hole 132 of the section 131 positioned next to the two grooves 133.

Like the upper open channel 1610, the interior surface of the lower open channel 1620 includes ridges or protrusions 1612, and a spring-loaded protrusion 1611. In alternative implementations, one or both of channels 1610 and 1620 may include at least two spring-loaded protrusions 1611. In alternative implementations, one or both of channels 1610 and 1620 may include an indentation or non-spring loaded protrusion in place of spring-load protrusion 1611.

Figure 17:
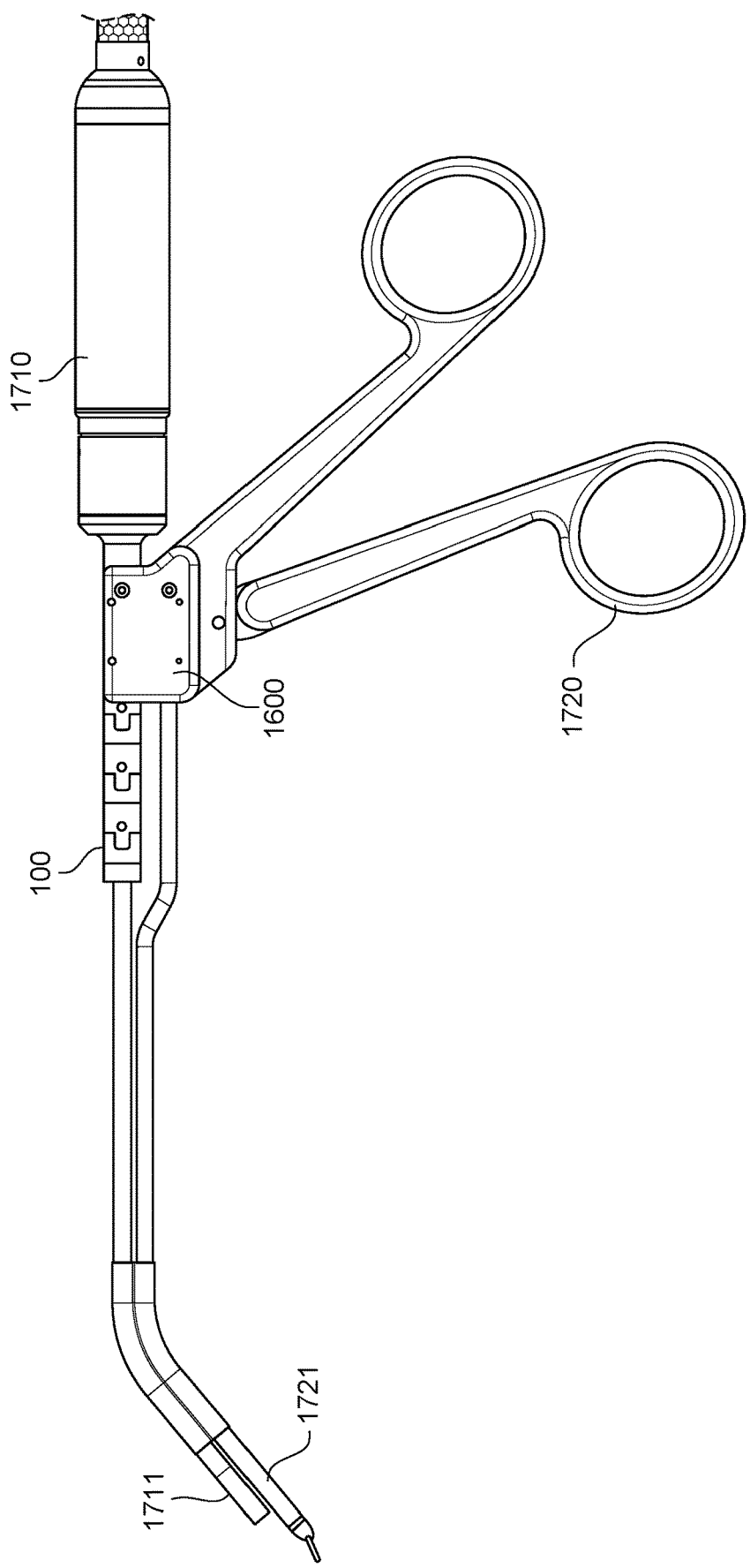
FIG. 17 shows a side view of an assembly including the H-channel adapter of FIG. 16A removably coupling an endoscope and forceps instrument, in accordance with some implementations of the disclosure.
Figure 18:
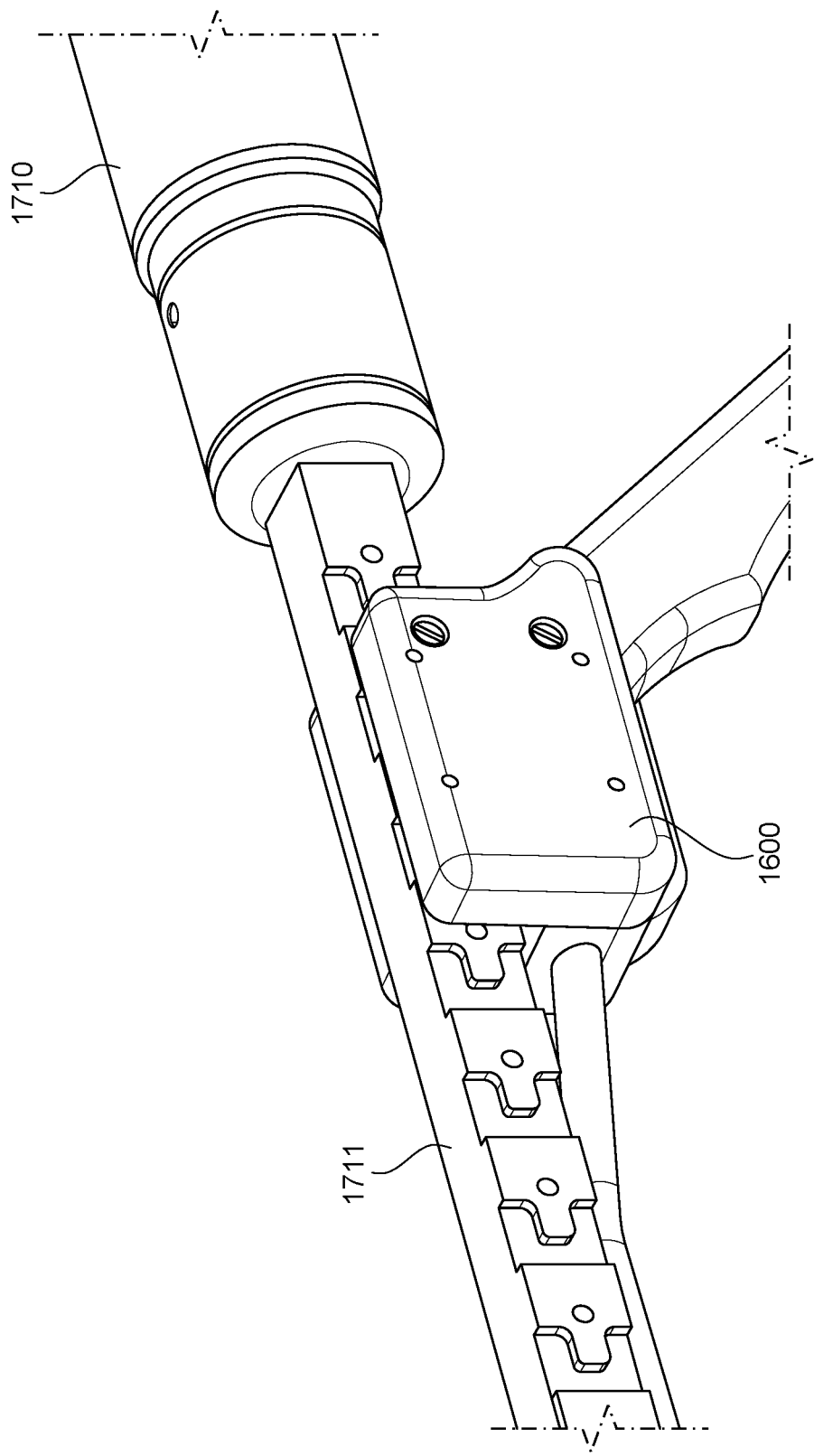
FIG. 18 shows a perspective view of the assembly of FIG. 17.

FIGS. 17-18 depict an H-channel adapter 1600 used to removably couple an endoscope 1710 and forceps instrument 1720, in accordance with implementations of the disclosure. FIG. 17 shows a side view. FIG. 18 shows a perspective view. As depicted, an endoscope attachment adapter 100 is coupled to endoscope 1710. The upper open channel 1610 of H-channel adapter 1600 is removably coupled to rigid attachment segment 130 of endoscope attachment adapter 100. The lower open channel 1620 of H-channel adapter 1600 is removably coupled to a handle portion of forceps instrument 1720. By virtue of using H-channel adapter 1600 to removably couple endoscope 1710 to forceps instrument 1720, a distal portion 1711 of endoscope 1710 may be conveniently positioned adjacent tool portion 1721 of forceps instrument 1720 to capture a suitable image of a patient's cavity. Moreover, a variety of other instruments may be removably coupled to the lower channel 1620 of H-channel adapter 1600.

Figure 19B:
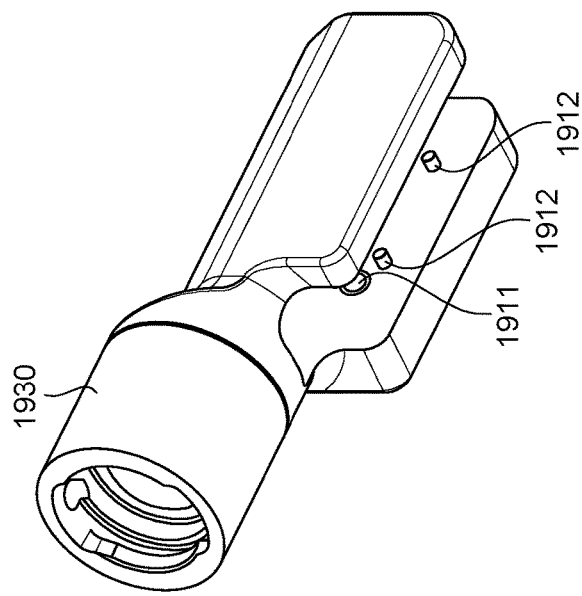
FIG. 19B shows another perspective view of the endoscope attachment adapter of FIG. 19A.
Figure 19D:
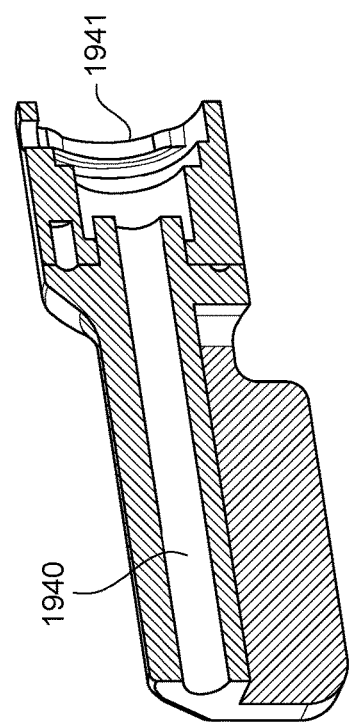
FIG. 19D shows another cross-sectional view of the endoscope attachment adapter of FIG. 19A.
Figure 19A:
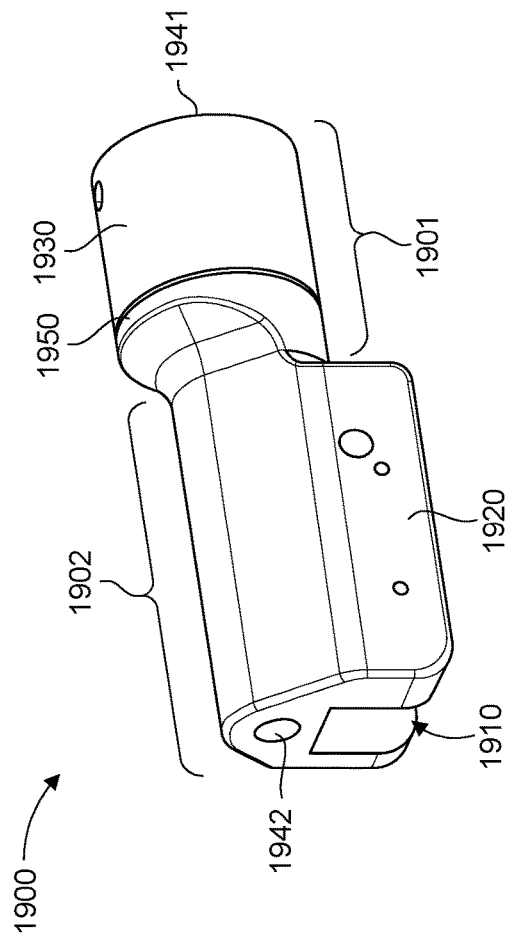
FIG. 19A shows a perspective view of an endoscope attachment adapter, in accordance with some implementations of the disclosure.
Figure 19C:
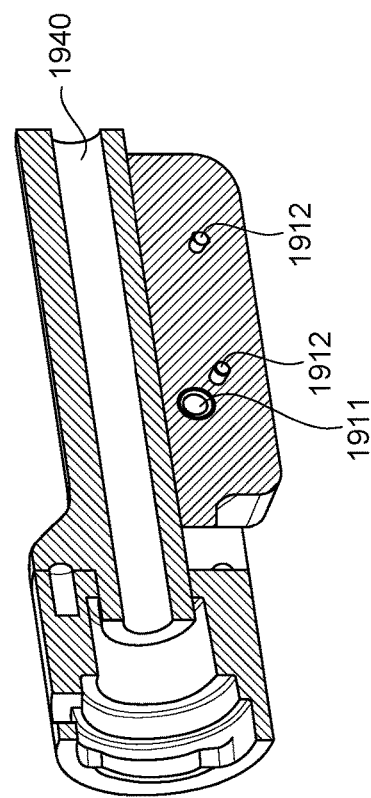
FIG. 19C shows a cross-sectional view of the endoscope attachment adapter of FIG. 19A.

FIGS. 19A-19D depict another implementation of an endoscope attachment adapter 1900, in accordance with implementations of the disclosure. FIGS. 19A-19B show different perspective views of the adapter 1900, and FIGS. 19C-19D show different cross-sectional views of adapter 1900. Adapter 1900 include a proximal part 1901 including an adapter connector 1930, and a distal part 1902 including a channel housing 1920 configured to couple to an instrument.

At a proximal end of adapter 1900 is an opening 1941 through connector 1930. At a distal end of adapter 100 is an opening 1942 through distal part 1902. From opening 1941 to opening 1942 is a channel 1940 that extends through connector 1930 and distal part 1902. To separate it from channel housing 1920, the channel 1940 may be closed. A shaft of an endoscope may be threaded through channel 1940, starting at opening 1941 and moving through opening 1942. Once the endoscope shaft is threaded through the channel of adapter 1900, adapter 1900 may be secured at a proximal end of the endoscope shaft by removably coupling adapter connector 1930 (e.g., to an endoscope connector). The two connectors may be secured and locked via one or more suitable coupling mechanisms, including a twist lock mechanism, an interference fit, a suction fit, a magnetic mechanism, and/or some other mechanism and then locked via mechanisms previously described. For example, a locking screw may be used to secure the connector 1930 to a male coupler of an endoscope. Although in this example connector 1930 is illustrated as a female coupler configured to connect to a male coupler (e.g., at a proximal end of an endoscope shaft), in other implementations connector 1930 may be a male coupler configured to connect to a female coupler (e.g., at a proximal end of an endoscope shaft).

Adapter 1900 includes a rotatable, circular joint 1950 that enables rotation of adapter 1900 about its longitudinal axis (e.g., rotation of rigid distal part 1902 relative to connector 1930). For example, the joint 1950 may be fused to an a proximal end of the rigid distal part 1902, and it may be structured and function in a manner similar to that discussed above with reference to joint 120. In this manner, an endoscope may be removably coupled to adapter 1900 in a plurality of different circumferential positions.

In this example, the channel housing 1920 of the distal part 1902 is positioned below channel 1940. Channel housing 1920 includes an open channel 1910. An interior surface of open channel 1910 includes ridges or protrusions 1912, and a spring-loaded protrusion (e.g., spring-loaded ball) 1911. Channel housing 1920 may be coupled to a rigid attachment segment having a structure similar to that described above with reference to rigid attachment segment 130.

Figure 20A:
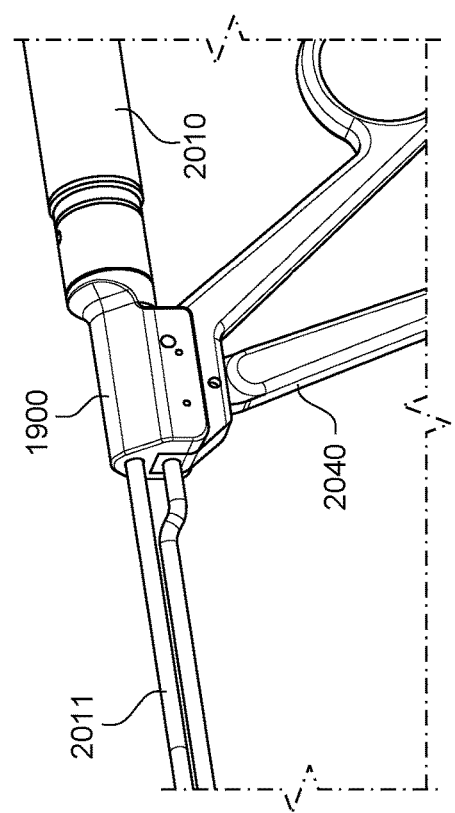
FIG. 20A shows a perspective view of an assembly including the endoscope attachment adapter of FIG. 19A removably coupling an endoscope and forceps instrument, in accordance with some implementations of the disclosure.
Figure 20B:
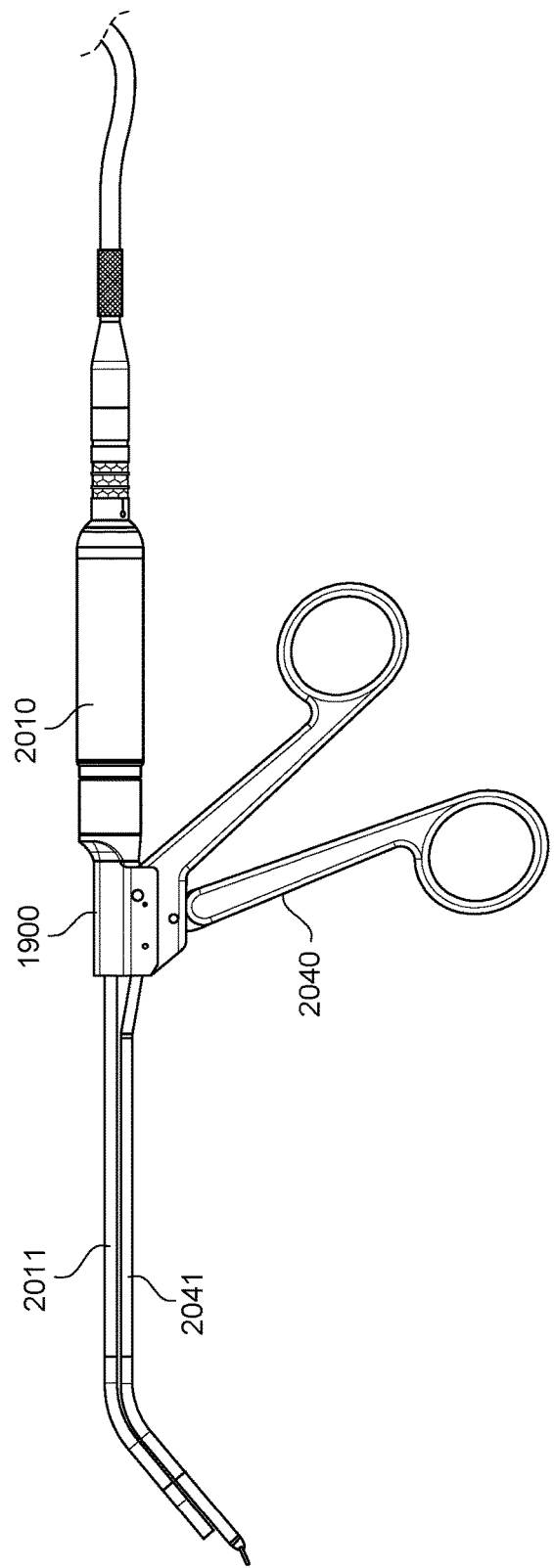
FIG. 20B shows a side view of the assembly of FIG. 20A.
Figure 21:
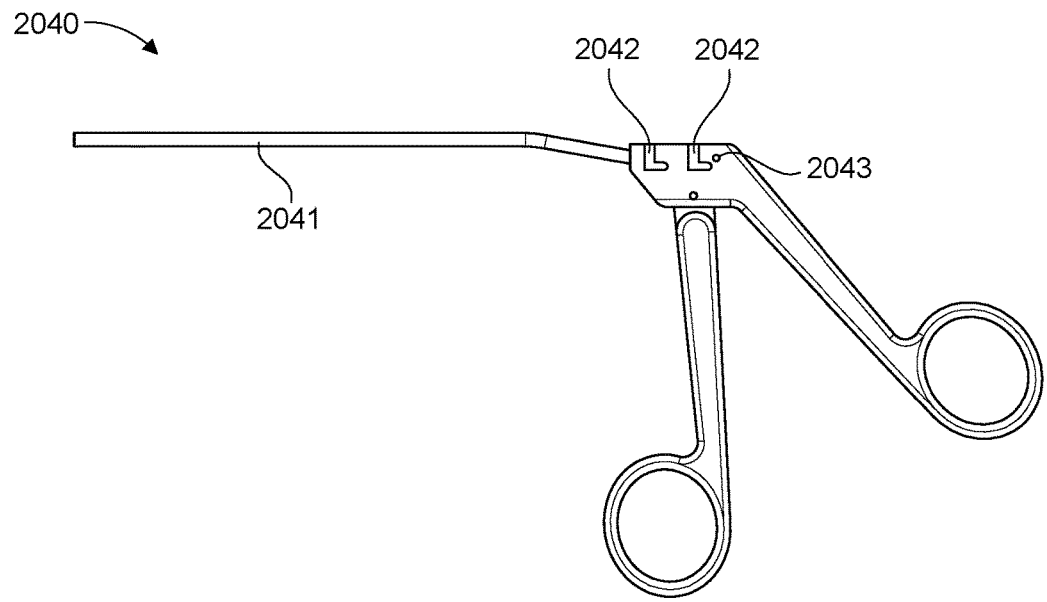
FIG. 21 shows a side view of the forceps instrument of the assembly of FIG. 20A, in accordance with some implementations of the disclosure.

FIGS. 20A-20B depict an endoscope attachment adapter 1900 used to removably couple an endoscope 2010 and forceps instrument 2040, in accordance with implementations of the disclosure. FIG. 20A shows a perspective view. FIG. 20B shows a side view. FIG. 21 depicts a side view of forceps instrument 2040. As depicted, adapter 1900 is removably coupled to endoscope 1900 by threading shaft 2011 of endoscope 2010 through channel 1940 (starting from opening 1941, and moving through opening 1942), and securing coupling adapter connector 1930 to endoscope 1900. For example, connector 1930 may be secured near a proximal end of shaft 2011 in a similar manner to that discussed above with reference to coupler 110.

Channel housing 1920 removably couples adapter 1900 to forceps instrument 2040 via open channel 1910 of adapter 1900. The open channel 1910 of adapter 1900 is removably coupled to a top of a handle portion of forceps instrument 2040, which includes grooves 2042 and indentation 2043 on its surface. The forceps instrument 2040 may be removably secured in place to open channel 1910 by i) pushing it into open channel 1910 along openings of the two grooves 2042; and ii) sliding the forceps handle relative to open channel 1910 to position each ridge 1912 within a respective groove 2042. Additionally, after sliding, spring-loaded protrusion 1911 may be secured within indentation/hole 2043.

By virtue of using adapter 1900 to removably couple endoscope 2010 to forceps instrument 2040, a distal portion of endoscope 2010 may be conveniently positioned adjacent tool portion 2041 of forceps instrument 2040 to capture a suitable image of a patient's cavity. Additionally, adapter 1900 effectually combines the upper channel of adapter 1600 with the rotational capability of adapter 100 while preserving the lower channel for instrument attachment.

Figure 22:
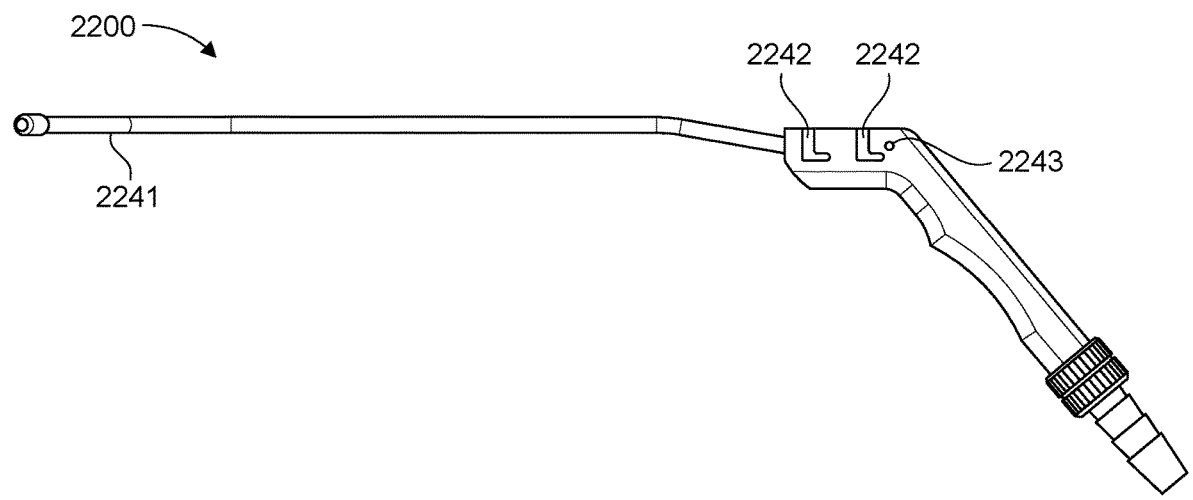
FIG. 22 shows a side view of a suction instrument that may be removably coupled to the endoscope attachment adapter of FIG. 19A, in accordance with some implementations of the disclosure.

Although FIGS. 20A-20B depict an endoscope attachment adapter 1900 used to removably couple an endoscope 2010 and forceps instrument 2040, it should be appreciated that adapter 1900 may couple a variety of different instruments to an endoscope, assuming the instruments have a coupling mechanism compatible with the attachment mechanism of open channel 1910. For example, FIG. 22 shows a suction instrument 2200 that may removably couple to adapter 1900 via open channel 1910. The suction instrument 2200 includes a handle portion and a tool portion 2241. Incorporated into a surface of a top of the handle portion are grooves 2242 and indentation 2243, which may be used to couple instrument 2200 to open channel 1910.

In certain implementations, it may be advantageous for the rigid proximal attachment segment (e.g., segment 130) of an endoscope adapter (e.g., adapter 100) threaded over a flexible shaft or endoscope shaft to include one or more hinges, allowing for changes in the shape of the endoscope shaft and adapter to accommodate varying shapes and contours of surgical instruments without allowing for flaccidity which would destabilize the scope when attached to an instrument. To this end, FIG. 23 depicts a portion of an endoscope shaft or attachment adapter 2300 that is rectangular and includes hinges 2310. In this implementation, hinges 2310 utilize an a joint that enables pivoting or rotation of portions of adapter 2300 about a single plane. FIG. 24 depicts a portion of an endoscope attachment adapter 2400 that is rectangular and includes a ball and socket hinge 2410. In this implementation, ball and socket hinge 2410 enables pivoting or rotation of portions of adapter 2400 about both a horizontal plane and vertical plane. Although FIGS. 23-24 illustrate two examples hinge joints that may be utilized, it should be appreciated that other suitable hinge joints may be used.

By virtue of utilizing a hinged adapter, different advantages may be realized depending on the instrument and application. For example, the head of the endoscope may be angled out of the way (e.g., 10-90 degrees) of the instrument. This may enable attachment of the endoscope to an instrument or device that itself must remain straight to function. As another example, the adapter may be hinged in two or three locations to bend the scope around the head of the instrument. Additionally, the hinged segments may enable attachment to various contours of instrumentation.

Figure 25A:
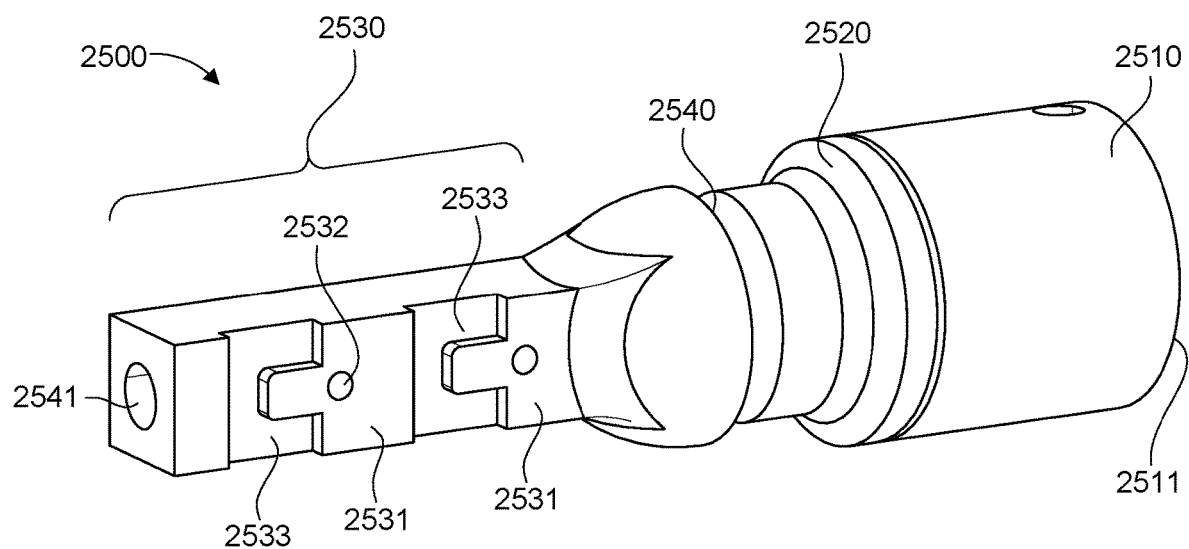
FIG. 25A shows a perspective view of another endoscope attachment adapter, in accordance with some implementations of the disclosure.
Figure 25B:
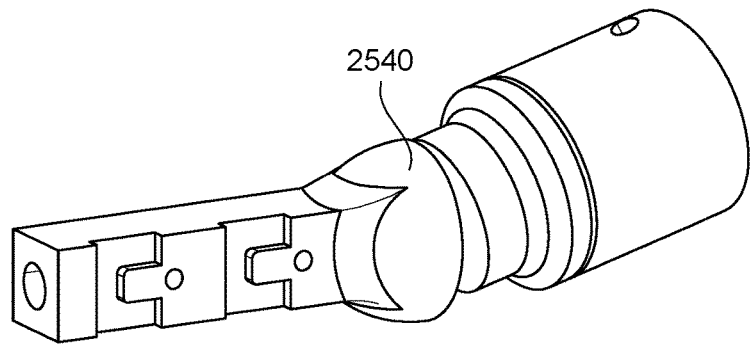
FIG. 25B shows a perspective view of the endoscope attachment adapter of FIG. 25A.
Figure 25C:
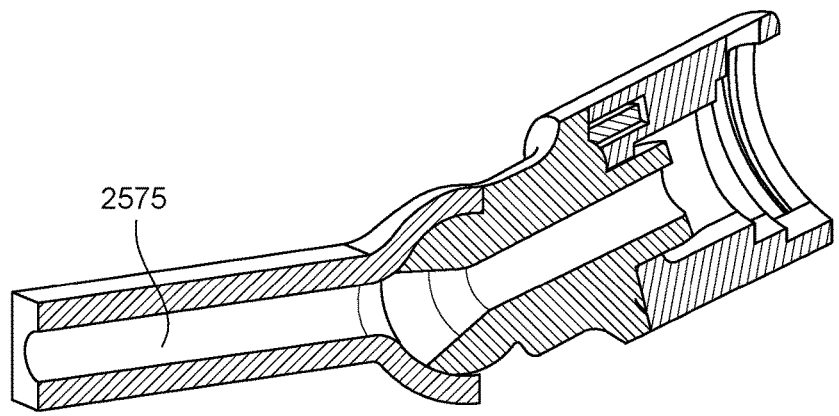
FIG. 25C shows a cross-sectional view of the endoscope attachment adapter of FIG. 25B.

FIGS. 25A-25C depict another embodiment of an endoscope attachment adapter 2500, in accordance with implementations of the disclosure. FIGS. 25A-25B illustrate a perspective view of adapter 2500, and FIG. 25C illustrates a cross-sectional view of adapter 2500. Adapter 2500 includes a coupler 2510, a rotatable joint 2520, a hinge joint 2540, and a rigid attachment segment 2530.

At a proximal end of adapter 2500 is an opening 2511 through connector 2510. At a distal end of adapter 2500 is an opening 2541. The opening 2541 may begin at a distal end of rigid attachment segment 2530. From opening 2511 to opening 2541 is a channel 2575 that extends through the length of adapter 2500. A flexible shaft of an endoscope may be threaded through channel 2575, starting at opening 2511 and moving through opening 2541. Once the endoscope shaft is threaded through the channel of adapter 2500, adapter 2500 may be secured at a proximal end of the endoscope shaft by removably coupling adapter connector 2510 (e.g., to an endoscope connector). The two connectors may be secured in a manner similar to that described above with reference to connector 110 of adapter 100.

Rigid attachment segment 2530 is four-sided with a square cross section. In other implementations, rigid attachment segment 2530 may have a different rectangular cross section or a circular cross-section. On the surface of one of the four sides of segment 2530 are formed a plurality of grooves/slots 2533 and a plurality of sections 2531 that protrude relative to the grooves 2533, each of the sections 2531 having a recessed indentation or hole 2532. Rigid attachment segment 2530 may be used to couple the adapter 2500 to an instrument in a manner similar to that discussed above with reference to adapter 100.

A rotatable joint 2520 positioned between hinge joint 2540 and coupler 2510 enables rotation of adapter 2500 about its longitudinal axis. Rotatable joint 2520 may be implemented in a manner similar to that discussed above with reference to rotatable joint 120. The hinge joint 2540 coupled between rigid attachment segment 2530 and coupler 2510 enables additional angling of rigid attachment segment 2530. By virtue of utilizing the combination of hinge joint 2540 and rotatable joint 2530 in this example, additional degrees of freedom in positioning adapter 2500 are provided. Adding several hinged joints 2540 in series allows for even greater changes in attachment shaft contour.

Figure 26:
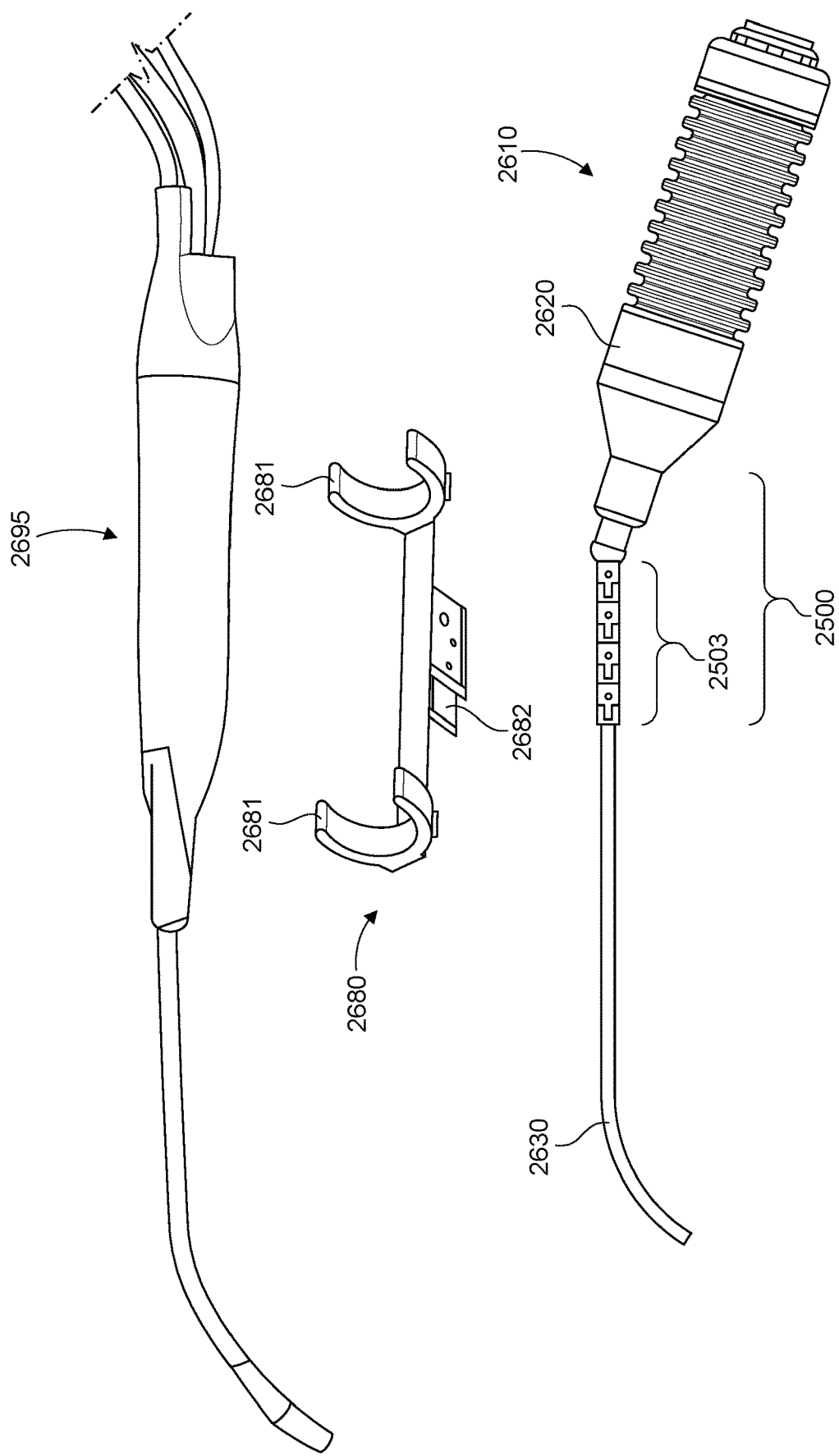
FIG. 26 shows a clip-on instrument adapter that connects to a hinged attachment adapter coupled to an endoscope, in accordance with some implementations of the disclosure.

FIG. 26 depicts a clip-on instrument adapter 2680 that connects to a hinged attachment adapter 2500 coupled to endoscope 2610 which is comprised of endoscope housing 2620 and flexible shaft 2630. Instrument adapter 2680 contains a channel housing 2682 that could be used to attach an endoscope attachment segment 2503. Additionally, instrument adapter 2680 includes one or more clips 2681 that may attach in various configurations to instrument housings and instrument configurations that do not have the necessary slot and groove configuration for direct attachment in the manner described above. For example, a body of ablation wand 2695 may be snapped on to clips 2681 in a specific position. Depending on the implementation of clip-on instrument adapter 2680, the clips 2681 may be manufactured to attach to different handles of different instruments of different manufacturers. Although this embodiment shows clips, other manners of attachment could also be used such as magnets, straps, clamps, screws, suction, cables, etc.

FIGS. 27A-27B show perspective and cross-sectional views of an endoscope attachment adapter 2700 with integrated cannula that may be used to flush/clean the tip of an endoscope. A suction/irrigation port 2720 would connect proximally via irrigation or suction tubing to a suction/irrigation pump activated by either foot or handheld control. On the distal undersurface of distal end 2740 of the cannula adapter 2700 there may be one or more instrument attachment connectors 2745 that are used to secure the adapter to an instrument shaft in one or more locations. Magnets incorporated within the cannula adapter or instrument shaft may also be used to attach the distal cannula adapter to the instrument shaft. In his example, the cannula adapter may slide over a rigid, flexible, or hybrid endoscope shaft and connect via connector 2710 to the endoscope coupler (FIG. 8A, 810) located on the distal endoscope housing, and may have rotation capabilities. The distal segment of the cannula, i.e., that portion of the cannula that extends distal from the rectangular attachment portion 2730 of the adapter, may also be rigid, flexible, or hybrid.

Figure 28:
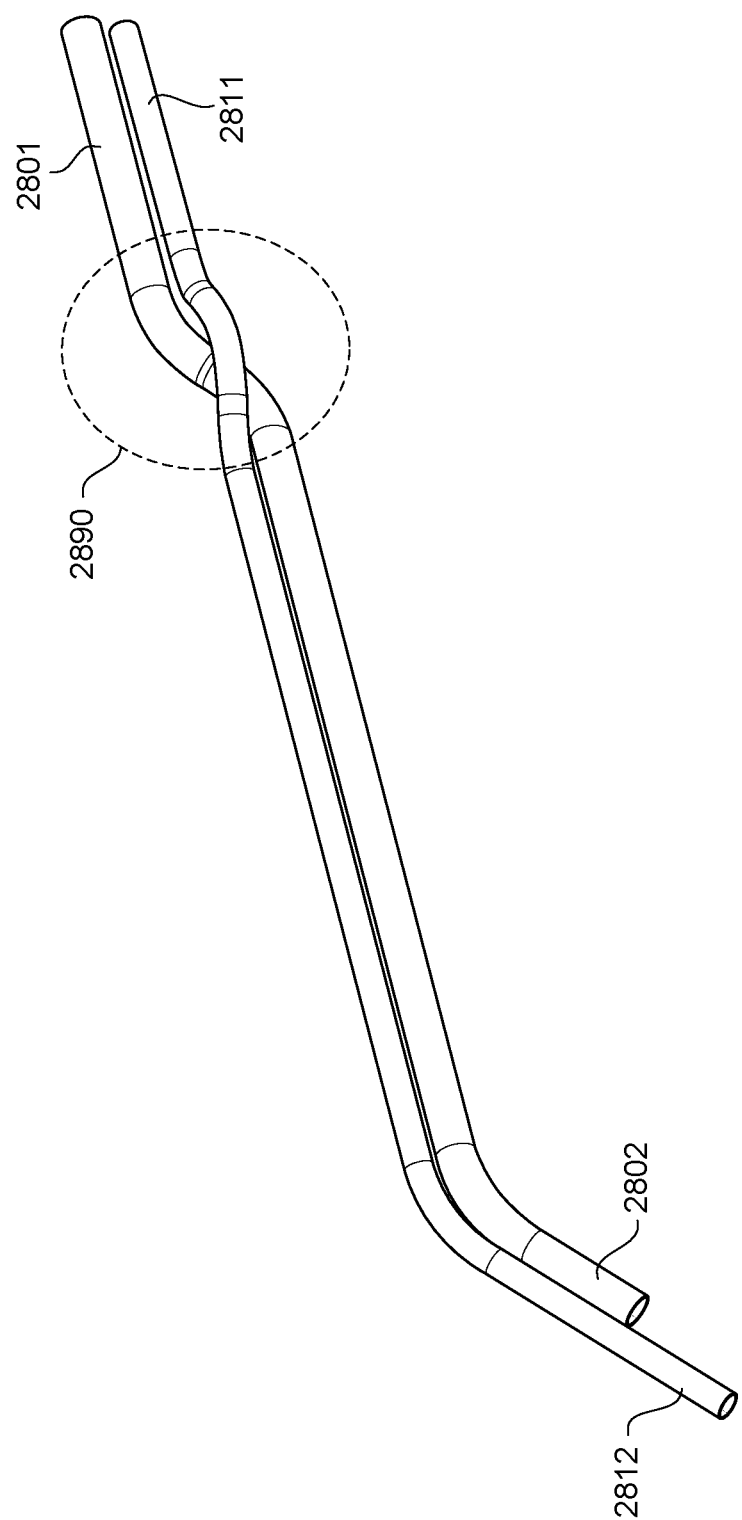
FIG. 28 depicts a corkscrew shaped instrument shaft, in accordance with some implementations of the disclosure.
Figure 29A:
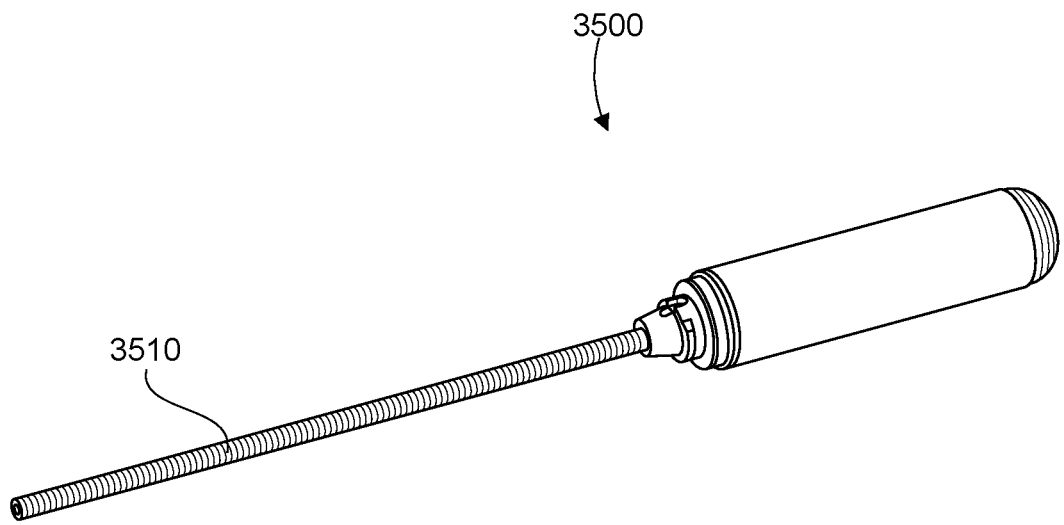
FIG. 29A shows a perspective view of an endoscope having a malleable shaft, in accordance with some implementations of the disclosure.
Figure 29B:
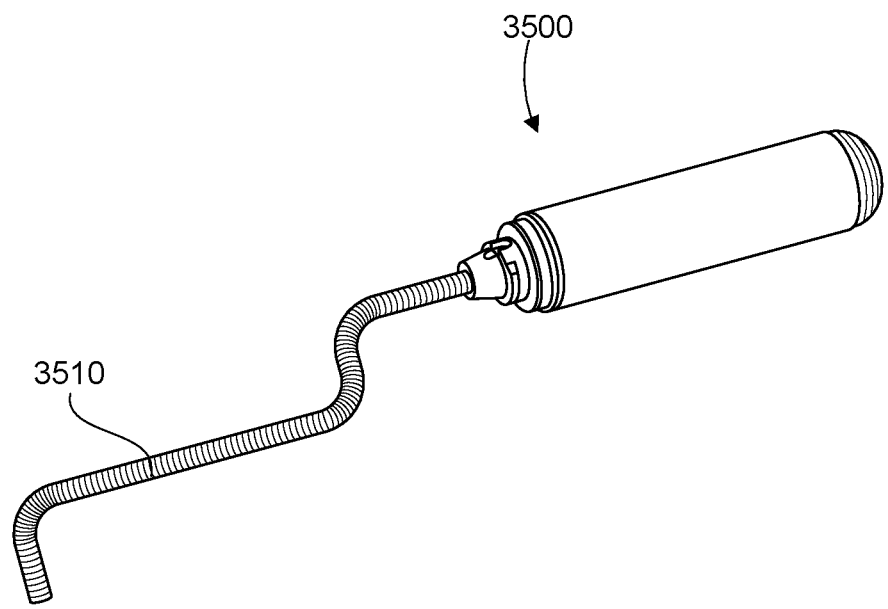
FIG. 29B shows the endoscope of FIG. 29A after bending the malleable shaft into a shape.
Figure 29C:
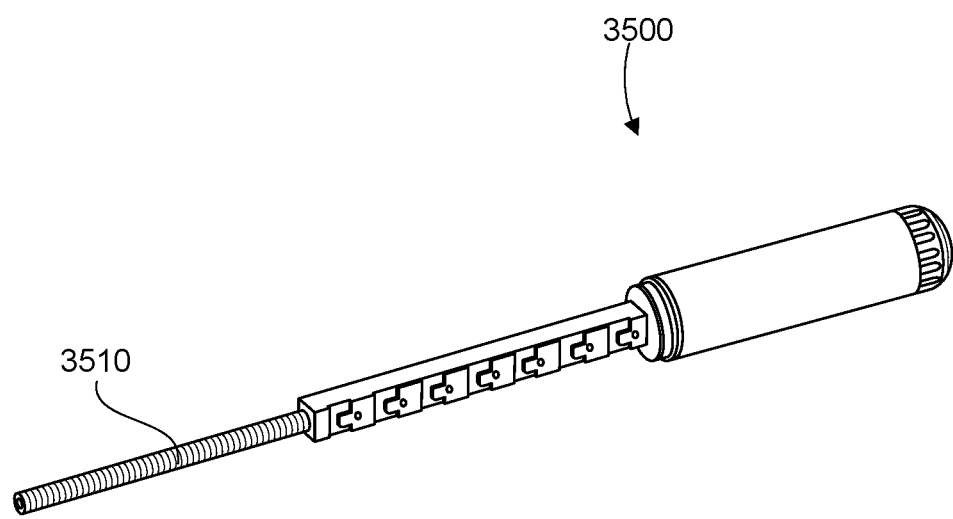
FIG. 29C shows the endoscope of FIG. 29A with a coupled endoscope attachment adapter.

FIG. 28 depicts a corkscrew shaped instrument shaft having a proximal end 2811 and distal end 2812. This shape may allow an endoscope shaft having proximal end 2801 positioned above instrument shaft proximal end 2811 to pass underneath the instrument shaft (e.g., at segment 2890) such that the distal end 2802 of the endoscope shaft is below distal end 2812 of the instrument shaft, allowing visualization by the endoscope of a tool tip of the instrument shaft from below rather than above the instrument shaft in a manner similar to the distal configuration of FIGS. 15A and 15B. A semi-rigid malleable endoscope shaft adapter that can be bent or molded around an instrument or instrument shaft in a reversible manner is also envisioned. Such an adapter could be used with an endoscope shaft that is malleable. For example, FIGS. 29A-29C depict one example of a an endoscope 3500 having a malleable endoscope shaft 3510. As illustrated by FIG. 29B the malleable endoscope shaft 3510 may be molded, bent, or otherwise shaped in a reversible manner. To accommodate the malleability of shaft 3510, the adapter, pictured in FIG. 29C may also be malleable.

Although embodiments have thus far been primarily described in the context of endoscope attachment adapters that removably couple to an endoscope and/or instrument used with an endoscope, it should be appreciated that some of the adapter implementations described herein and their associated technical advantages may be realized by directly incorporating their features directly into an endoscope and/or endoscope instrument, whether disposable or reusable. For example, a flexible-rigid hybrid endoscope (e.g., an endoscope having a shaft with a flexible distal end and a rigid proximal end) or a rigid endoscope (e.g., an endoscope having a rigid shaft) may have an endoscope shaft with an integrated proximal attachment segment similar in structural features to adapter 100, adapter 200, adapter 900, adapter 1000, adapter 1900, adapter 2500, or adapter 2700. In such implementations, since the structural features of the adapter are incorporated into the endoscope (e.g., at the proximal end of the endoscope shaft), the endoscope connector (e.g., 110) of the adapter may be excluded.

For example, the proximal segment of the endoscope shaft may have a rectangular cross section, similar to the one described above for adapter 100, on which on at least one of the four sides are formed a plurality of grooves/slots 133 and a plurality of sections 131, each of the sections 131 having a recessed indentation or hole 132. In such implementations, the benefits of this top-down ratchet attachment design may be realized by directly integrating them into the proximal attachment segment of the endoscope shaft. Additionally, the endoscope shaft may be configured to rotate about a rotatable joint. Furthermore, the endoscope shaft may be configured to couple to instrument housing 1100, instrument housing 1200, or H-channel adapter 1300, or H-channel adapter 1600. Moreover, the proximal attachment segment of the endoscope shaft may itself include one or more hinges, allowing for changes in the shape of the endoscope shaft to accommodate varying shapes and contours of surgical instruments without allowing for flaccidity which would destabilize the scope when attached to an instrument.

The endoscopes, attachment mechanisms, and instruments described herein may be utilized in any suitable application. For example, they may be utilized in Otorhinolaryngologic (Ear, nose, and throat, ENT) surgical applications. They may also be utilized in other surgical and medical specialties such as general surgery, gastroenterology, pulmonology, urology, plastic surgery, neurosurgery, OB/GYN, and orthopedics for applications such as surgical stapling, tissue ablation, arthroscopic surgery, etc. Commercial, non-surgical, applications for the technology disclosed herein are also applicable.

Although described above in terms of various example implementations, it should be understood that the various features, aspects and functionality described in one or more of the individual implementations are not limited in their applicability to the particular implementation with which they are described, but instead can be applied, alone or in various combinations, to one or more of the other implementations of the application, whether or not such implementations are described and whether or not such features are presented as being a part of a described implementation. Thus, the breadth and scope of the present application should not be limited by any of the above-described example implementations.

The terms "substantially" and "about" used throughout this disclosure, including the claims, are used to describe and account for small fluctuations, such as due to variations in processing. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

To the extent applicable, the terms "first," "second," "third," etc. herein are merely employed to show the respective objects described by these terms as separate entities and are not meant to connote a sense of chronological order, unless stated explicitly otherwise herein.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide some instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various implementations set forth herein are described in terms of example block diagrams, flow charts and other illustrations. As will become apparent to one of ordinary skill in the art after reading this document, the illustrated implementations and their various alternatives can be implemented without confinement to the illustrated examples. For example, block diagrams and their accompanying description should not be construed as mandating a particular architecture or configuration.

While various implementations of the present disclosure have been described above, it should be understood that they have been presented by way of example only, and not of limitation. Likewise, the various diagrams may depict an example architectural or other configuration for the disclosure, which is done to aid in understanding the features and functionality that can be included in the disclosure. The disclosure is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present disclosure. Also, a multitude of different constituent module names other than those depicted herein can be applied to the various partitions. Additionally, with regard to flow diagrams, operational descriptions and method claims, the order in which the steps are presented herein shall not mandate that various implementations be implemented to perform the recited functionality in the same order unless the context dictates otherwise.

What is claimed is:

1. An endoscope, comprising:
a shaft comprising:
    a distal end; and
    a proximal end comprising a rigid attachment segment configured to be removably coupled to an adapter or instrument, a first surface of the rigid attachment segment comprising a first groove and a first section adjacent the first groove, wherein:
        the first groove is configured to be engaged by a protrusion of the adapter or the instrument,
        the first section protrudes relative to the first groove, and
        the first section comprises a first recessed indentation configured to secure a spring-loaded ball of the adapter or the instrument; and
a housing coupled to the shaft.

2. The endoscope of claim 1, wherein:
the first surface of the rigid attachment segment comprises a first plurality of grooves and a first plurality of sections alternating along a longitudinal length of the rigid attachment segment, the first plurality of grooves including the first groove, and the first plurality of sections including the first section;
each of the first plurality of sections protrudes relative to the first plurality of grooves, and comprises a recessed indentation; and
the first plurality of sections and the first plurality of grooves are configured such that the instrument or the adapter can be coupled to the endoscope in a plurality of lengthwise positions.

3. The endoscope of claim 2, wherein:
the rigid attachment segment has at least two different surfaces running along the longitudinal length of the rigid attachment segment, the at least two different surfaces including the first surface and a second surface;
the second surface comprises a second plurality of grooves and a second plurality of sections alternating along the longitudinal length of the rigid attachment segment;
each of the second plurality of sections protrudes relative to the second plurality of grooves, and comprises a recessed indentation; and
the second plurality of sections and the second plurality of grooves are configured such that the instrument or the adapter can be coupled to the endoscope in a plurality of lengthwise positions.

4. The endoscope of claim 1, further comprising: a rotatable joint attached to the rigid attachment segment and configured to enable longitudinal rotation of the rigid attachment segment relative to the housing.

5. The endoscope of claim 1, wherein:
the rigid attachment segment has at least two different surfaces running along a longitudinal length of the rigid attachment segment, the at least two different surfaces including the first surface and a second surface; and
the second surface comprises a second groove and a second section adjacent the second groove, the second section protruding relative to the second groove, and comprising a second recessed indentation.

6. The endoscope of claim 1, further comprising: a rotatable control positioned at a proximal end of the endoscope, the rotatable control configured to be rotated to digitally adjust an orientation of an image captured by the endoscope.

7. The endoscope of claim 1, wherein the rigid attachment segment comprises a hinged joint between two portions of the rigid attachment segment, the hinged joint configured to enable pivoting or rotation of at least one of the two portions about at least one plane.

8. The endoscope of claim 1, further comprising: a hinged joint between the rigid attachment segment and the housing, the hinged joint configured to enable pivoting or rotation of the rigid attachment segment.

9. The endoscope of claim 1, further comprising: a cannula integrated into the shaft, the cannula comprising a suction or irrigation port.

10. The endoscope of claim 1, further comprising: a rotatable joint attached to the rigid attachment segment and configured to enable longitudinal rotation of the rigid attachment segment.

11. An endoscope assembly, comprising:
an endoscope, comprising:
a shaft comprising:
a distal end; and
a proximal end comprising a rigid attachment segment configured to be removably coupled to an adapter or instrument, a first surface of the rigid attachment segment comprising a first groove and a first section adjacent the first groove, wherein:
the first groove is configured to be engaged by a protrusion of the adapter or the instrument,
the first section protrudes relative to the first groove, and
the first section comprises a first recessed indentation configured to secure a spring-loaded ball of the adapter or the instrument; and
a housing coupled to the shaft; and
the adapter or the instrument.

12. The endoscope assembly of claim 11, wherein:
the first surface of the rigid attachment segment comprises a first plurality of grooves and a first plurality of sections alternating along a longitudinal length of the rigid attachment segment;
each of the first plurality of sections protrudes relative to the first plurality of grooves, and comprises a recessed indentation; and
the first plurality of sections and the first plurality of grooves are configured such that the instrument or the adapter can be coupled to the endoscope in a plurality of lengthwise positions.

13. The endoscope assembly of claim 11, comprising: the adapter, the adapter including:
a first channel configured to be removably coupled to the rigid attachment segment, and
a second channel configured to be removably coupled to an instrument.

14. The endoscope assembly of claim 13, wherein an interior surface of the first channel comprises the protrusion configured to engage the first groove, and the spring-loaded ball configured to engage the first recessed indentation of the first section.

15. The endoscope assembly of claim 14, wherein:
the interior surface of the first channel further comprises another protrusion and another spring-loaded ball;
the first surface of the rigid attachment segment further comprises a second groove and a second section adjacent the second groove;
the second groove is configured to be engaged by the other protrusion; and
the second section comprises a second recessed indentation configured to secure the other spring-loaded ball.

16. The endoscope assembly of claim 13, wherein:
the adapter is an H-channel adapter,
one of the first channel and the second channel is a top open channel of the H-channel adapter, and
one of the first channel and the second channel is a lower open channel of the H-channel adapter.

17. The endoscope assembly of claim 11, comprising: the instrument, the instrument comprising a channel configured to be removably coupled to the rigid attachment segment.

18. The endoscope assembly of claim 17, wherein an interior surface of the channel comprises the protrusion configured to engage the first groove, and the spring-loaded ball configured to engage the first recessed indentation of the first section.

19. The endoscope assembly of claim 11, further comprising: a rotatable control positioned at a proximal end of the endoscope, the rotatable control configured to be rotated to digitally adjust an orientation of an image captured by the endoscope.

20. The endoscope assembly of claim 11, comprising: the adapter, the adapter including:
a first channel configured to be removably coupled to the rigid attachment segment, and
a second channel comprising a plurality of clips configured to be removably coupled to an instrument.

* * * * *